United States Patent
Patel et al.

(10) Patent No.: US 9,538,996 B2
(45) Date of Patent: Jan. 10, 2017

(54) FISTULA GRAFTS AND RELATED METHODS AND SYSTEMS FOR TREATING FISTULAE

(75) Inventors: Umesh H. Patel, West Lafayette, IN (US); F. Joseph Obermiller, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1776 days.

(21) Appl. No.: 11/669,695

(22) Filed: Jan. 31, 2007

(65) Prior Publication Data
US 2007/0198059 A1 Aug. 23, 2007

Related U.S. Application Data

(60) Provisional application No. 60/763,521, filed on Jan. 31, 2006.

(51) Int. Cl.
*A61B 17/08* (2006.01)
*A61B 17/00* (2006.01)
(Continued)

(52) U.S. Cl.
CPC .......... *A61B 17/0057* (2013.01); *A61B 50/30* (2016.02); *A61L 27/3604* (2013.01);
(Continued)

(58) Field of Classification Search
CPC .......... A61B 2017/00641; A61B 2017/00654; A61B 17/12159; A61B 2017/00628; A61B 17/0057; A61B 2017/00004; A61B 17/3468; A61B 2017/00862; A61B 2017/22038; A61B 2017/00867; A61B 2017/00659; A61B 1/31; A61B 50/30; A61L 27/3604; A61L 27/3641
(Continued)

(56) References Cited

U.S. PATENT DOCUMENTS

| 2,127,903 A | 8/1938 | Bowen |
| 3,054,406 A * | 9/1962 | Usher .................. 606/151 |

(Continued)

FOREIGN PATENT DOCUMENTS

| EP | 1570788 | 9/2005 |
| EP | 1671591 | 6/2006 |

(Continued)

OTHER PUBLICATIONS

Himpson, Rebecca C., et al. "Histological evidence for enhanced anal fistula repair using autologous fibroblasts in a dermal collagen matrix". Comparative Clinical Pathology, Apr. 2006, vol. 16, No. 1.
(Continued)

*Primary Examiner* — Jing Ou
(74) *Attorney, Agent, or Firm* — Woodard, Emhardt, Moriarty, McNett & Henry LLP

(57) ABSTRACT

Described are medical graft products, systems, and methods for treating fistulae. Certain products of the invention are configured to have portions residing in and around a primary fistula opening, e.g., one occurring in a wall of the alimentary canal. One such product includes a biocompatible graft body which is configured to block at least the primary opening. The graft body includes a capping member, which is configured to contact portions of the alimentary canal wall adjacent to the primary opening, and an elongate plug member extending from the capping member, which is configured to extend into at least a portion of the fistula. In certain embodiments, a graft body component has the capacity to expand or otherwise change form to provide a suitable capping arrangement. Such a component can include a resilient wire frame, e.g., one that is self-expandable or one that requires at least some manipulation in order to expand.

61 Claims, 9 Drawing Sheets

(51) Int. Cl.
*A61L 27/36* (2006.01)
*A61B 17/12* (2006.01)
*A61B 1/31* (2006.01)
*A61B 17/34* (2006.01)
*A61B 17/22* (2006.01)

(52) U.S. Cl.
CPC ............ *A61L 27/3641* (2013.01); *A61B 1/31* (2013.01); *A61B 17/12159* (2013.01); *A61B 17/3468* (2013.01); *A61B 2017/00004* (2013.01); *A61B 2017/00628* (2013.01); *A61B 2017/00641* (2013.01); *A61B 2017/00654* (2013.01); *A61B 2017/00659* (2013.01); *A61B 2017/00862* (2013.01); *A61B 2017/00867* (2013.01); *A61B 2017/22038* (2013.01)

(58) Field of Classification Search
USPC ....... 623/23.64, 23.65, 23.72, 1.23; 606/139, 606/213
See application file for complete search history.

(56) References Cited

U.S. PATENT DOCUMENTS

| | | | |
|---|---|---|---|
| 3,707,150 A * | 12/1972 | Montgomery et al. | 606/151 |
| 4,511,653 A | 4/1985 | Play et al. | |
| 4,744,364 A | 5/1988 | Kensey | |
| 4,852,568 A | 8/1989 | Kensey | |
| 4,854,316 A * | 8/1989 | Davis | 606/153 |
| 4,902,508 A | 2/1990 | Badylak et al. | |
| 4,956,178 A | 9/1990 | Badylak et al. | |
| 4,981,465 A | 1/1991 | Ballan | |
| 5,061,274 A | 10/1991 | Kensey | |
| 5,116,357 A * | 5/1992 | Eberbach | 606/213 |
| 5,147,374 A * | 9/1992 | Fernandez | 606/151 |
| 5,192,302 A | 3/1993 | Kensey et al. | |
| 5,275,616 A * | 1/1994 | Fowler | 606/213 |
| 5,275,826 A | 1/1994 | Badylak et al. | |
| 5,281,422 A | 1/1994 | Badylak et al. | |
| 5,334,216 A | 8/1994 | Vidal | |
| 5,366,460 A * | 11/1994 | Eberbach | 606/151 |
| 5,374,261 A | 12/1994 | Yoon | |
| RE34,866 E | 2/1995 | Kensey et al. | |
| 5,397,331 A * | 3/1995 | Himpens et al. | 606/151 |
| 5,516,533 A | 5/1996 | Badylak et al. | |
| 5,554,389 A | 9/1996 | Badylak et al. | |
| 5,584,827 A | 12/1996 | Korteweg | |
| 5,620,461 A | 4/1997 | Muijs Van De Moer | |
| 5,628,762 A | 5/1997 | Moshin | |
| 5,643,305 A | 7/1997 | Moshin | |
| 5,752,974 A | 5/1998 | Rhee | |
| 5,755,791 A | 5/1998 | Whitson et al. | |
| 5,955,110 A | 9/1999 | Patel et al. | |
| 5,993,844 A | 11/1999 | Abraham et al. | |
| 5,997,575 A | 12/1999 | Whitson et al. | |
| 6,090,996 A | 7/2000 | Li | |
| 6,099,567 A | 8/2000 | Badylak et al. | |
| 6,113,623 A * | 9/2000 | Sgro | 606/215 |
| 6,206,931 B1 | 3/2001 | Cook et al. | |
| 6,241,768 B1 * | 6/2001 | Agarwal et al. | 623/11.11 |
| 6,315,787 B1 | 11/2001 | Tsugita | |
| 6,375,989 B1 | 4/2002 | Badylak et al. | |
| 6,569,081 B1 * | 5/2003 | Nielsen et al. | 600/32 |
| 6,666,892 B2 | 12/2003 | Hiles et al. | |
| 6,837,894 B2 * | 1/2005 | Pugsley et al. | 606/139 |
| 7,101,381 B2 * | 9/2006 | Ford et al. | 606/151 |
| 7,377,929 B2 * | 5/2008 | Crawley et al. | 606/151 |
| 7,819,797 B2 * | 10/2010 | Vanden Hoek et al. | 600/37 |
| 2001/0027347 A1 * | 10/2001 | Rousseau | 623/23.72 |
| 2001/0039450 A1 * | 11/2001 | Pavcnik et al. | 623/1.24 |
| 2003/0013989 A1 | 1/2003 | Obermiller et al. | |
| 2003/0051735 A1 * | 3/2003 | Pavcnik et al. | 128/831 |
| 2004/0087980 A1 * | 5/2004 | Ford et al. | 606/151 |
| 2004/0158185 A1 | 8/2004 | Moran et al. | |
| 2004/0176798 A1 | 9/2004 | Epstein et al. | |
| 2005/0013844 A1 | 1/2005 | Hadlock et al. | |
| 2005/0049626 A1 | 3/2005 | Burgard | |
| 2005/0070759 A1 | 3/2005 | Armstrong | |
| 2005/0155608 A1 | 7/2005 | Pavcnik et al. | |
| 2005/0159776 A1 | 7/2005 | Armstrong et al. | |
| 2005/0182495 A1 * | 8/2005 | Perrone | 623/23.72 |
| 2006/0015142 A1 | 1/2006 | Malazgirt | |
| 2007/0031508 A1 | 2/2007 | Armstrong et al. | |
| 2007/0088445 A1 | 4/2007 | Patel et al. | |

FOREIGN PATENT DOCUMENTS

| | | | |
|---|---|---|---|
| RU | 2180529 C2 | 3/2002 | |
| SU | 1673130 | 8/1991 | |
| SU | 1690737 | 11/1991 | |
| SU | 1718837 | 3/1992 | |
| WO | WO 93/07813 | 4/1993 | |
| WO | WO 98/22158 | 5/1998 | |
| WO | WO 98/25637 | 6/1998 | |
| WO | WO 00/19912 | 4/2000 | |
| WO | 2000/72759 A2 | 12/2000 | |
| WO | WO 03/022158 | 3/2003 | |
| WO | WO 2004/012627 | 2/2004 | |
| WO | WO 2004024030 A1 * | 3/2004 | ............ A61F 2/00 |
| WO | 2005/020823 A1 | 3/2005 | |
| WO | WO 2005/020847 | 3/2005 | |
| WO | WO 2006/119256 | 11/2006 | |
| WO | WO 2007/002260 | 1/2007 | |

OTHER PUBLICATIONS

Khairy, G. E. A., et al. "Percutaneous obliteration of duodenal fistula". J.R. Coll. Surg. Edinb., 45, Oct. 2000, 342-344.

Lisle, David A., et al. "Percutaneous Gelfoam Embolization of Chronic Enterocutaneous Fistulas: Report of Three Cases". Diseases of the Colon & Rectum, vol. 50, No. 2, Dec. 2006.

Maluf-Filho, F. et al. "Endoscopic Treatment of Esophagogastric Fistulae with an Acellular Matrix". Gastrointestinal Endoscopy, Elsevier, NL, vol. 59, No. 5, Apr. 2004 (Apr. 2004), p. 151, XP004854594 abstract.

Moore, Robert D., et al. "Rectovaginal Fistula Repair Using a Porcine Dermal Graft". Obstetrics & Gynecology, 2004, 104, 1165-1167.

Schwesinger, Wayne H., "Management of Persistent Fistula After Gastrectomy" on-line question (www.medscape.com), posted on May 14, 2002.

Shah, A. M., et al. "Bronchoscopic closure of bronchopleural fistula using gelfoam" abstract. Journal of Association of Physicians of India, 2004, vol. 52, no JUIN, pp. 508-509.

Shaker MA, Hindy AM, Mounir RM, Geaisa KM. Egypt Dent J. Jul. 1995; 41(3): 1237-42.

Sheiman, Robert G., et al. "Percutaneous Treatment of a Pancreatic Fistula after Pancreaticoduodenectomy". J Vasc Interv Radiol, 2001, vol. 12, No. 4, pp. 524-526.

U.S. Appl. No. 11/766,606, filed Jun. 6, 2007 to Obermiller et al.

Wilson Gunn on behalf of unnamed party, Letter to the European Patent Office, Jan. 30, 2007, pp. 1-4.

PCT/US2007/061371International Search Report, 7 pages.

PCT/US2007/061371Written Opinion, 18 pages.

U.S. Appl. No. 11/415,403, filed May 1, 2006, Volumetric Grafts for Treatment of Fistulae and Related Methods and Systems.

U.S. Appl. No. 11/669,709, filed Jan. 31, 2007, Fistula Graft Deployment Systems and Methods.

Heeschen, C., et al. "Nicotine Stimulates Angiogenesis and Promotes Tumor Growth and Atherosclerosis". Nature Medicine, vol. 7., No. 7, Jul. 2001. pp. 833-839.

Johnson, C., et al. "Matrix Metalloproteinase-9 is Required for Adequate Angiogenic Revascularization of Ischemic Tissues: Potential Role in Capillary Branching". Circulation Research, vol. 94. (2004) pp. 262-268.

Miklos, J. R., et al. "Rectovaginal Fistula Repair Utilizing a Cadaveric Dermal Allograft". International Urogynecology Journal, 1999, vol. 10, No. 6, pp. 405-406.

(56) References Cited

OTHER PUBLICATIONS

Schultz, David J., et al. "Porcine Small Instestine Submucosa as a Treatment for Enterocutaneous Fistulas". Journal of American College of Surgeons, 2002, vol. 194, No. 4, Apr. 2002, pp. 541-543.
Shelton, Andrew A., et al., "Transperineal Repair of Persistent Rectovaginal Fistulas Using an Acellular Cadaveric Dermal Graft (AlloDerm)", Diseases of the Colon & Rectum, 2006, vol. 49, No. 9, pp. 1454-1457.

* cited by examiner

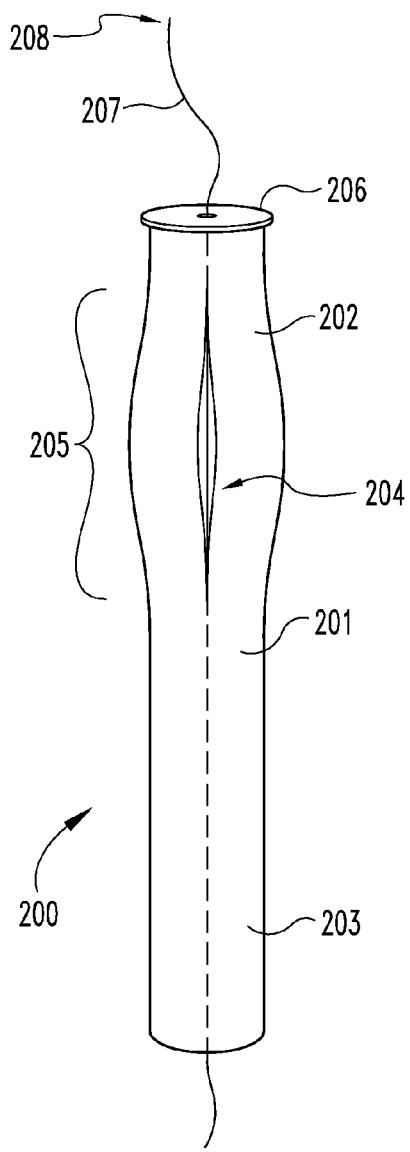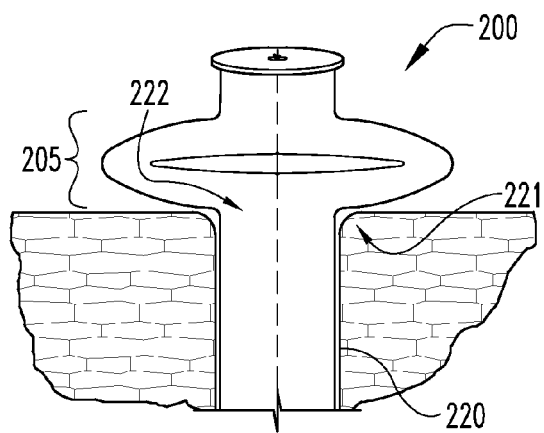
Fig. 12A
Fig. 12B

FISTULA GRAFTS AND RELATED METHODS AND SYSTEMS FOR TREATING FISTULAE

REFERENCE TO RELATED APPLICATIONS

The present application claims the benefit of United States Provisional Patent Application Ser. No. 60/763,521 filed Jan. 31, 2006 entitled "FISTULA GRAFTS AND RELATED METHODS AND SYSTEMS FOR TREATING FISTULAE" which is hereby incorporated by reference in its entirety.

BACKGROUND

The present invention relates generally to medical devices and in particular aspects to medical products and methods for treating fistulae including those having a primary opening in the alimentary canal.

As further background, a variety of fistulae can occur in humans. These fistulae can occur for a variety of reasons, such as but not limited to, as a congenital defect, as a result of inflammatory bowel disease, such as Chron's disease, irradiation, trauma, such as childbirth, or as a side effect from a surgical procedure. Further, several different types of fistulae can occur, for example, urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

Anorectal fistulae can result from infection in the anal glands, which are located around the circumference of the distal anal canal that forms the anatomic landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings.

The path which these fistulae take, and their complexity, can vary. A fistula may take a take a "straight line" path from the primary to the secondary opening, known as a simple fistula. Alternatively, the fistula may consist of multiple tracts ramifying from the primary opening and have multiple secondary openings. This is known as a complex fistula.

The anatomic path which such fistulae take is classified according to their relationship to the anal sphincter muscles. The anal sphincter consists of two concentric bands of muscle, the inner or internal sphincter and the outer or external anal sphincter. Fistulae which pass between the two concentric anal sphincters are known as inter-sphincteric fistulae. Those which pass through both internal and external sphincters are known as trans-sphincteric fistulae, and those which pass above both sphincters are called supra-sphincteric fistula. Fistulae resulting from Crohn's disease usually "ignore" these anatomic planes, and are known a "extra-anatomic" fistulae.

Many complex fistulae consist of multiple tracts, some blind-ending and others leading to multiple secondary openings. One of the most common complex fistulae is known as a horseshoe fistula. In this instance, the infection starts in the anal gland (primary opening) at or near the 12 o'clock location (with the patient in the prone position). From this primary opening, fistulae pass bilaterally around the anal canal, in a circumferential manner. Multiple secondary openings from a horseshoe fistula may occur anywhere around the periphery of the anal canal, resulting in a fistula tract with a characteristic horseshoe configuration.

One technique for treating a perianal fistulae is to make an incision adjacent the anus until the incision contacts the fistula and then excise the fistula from the anal tissue. This surgical procedure tends to sever the fibers of the anal sphincter, and may cause incontinence.

Other surgical treatment of fistulae involve passing a fistula probe through the tract of the fistula in a blind manner, using primarily only tactile sensation and experience to guide to probe. Having passed the probe through the fistula tract, the overlying tissue is surgically divided. This is known as a fistulotomy. Since a variable amount of sphincter muscle is divided during the procedure, fistulotomy also may result in impaired sphincter control, and even frank incontinence.

Still other methods involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and to allow the fistula tract to "mature" prior to injecting a sealant. If sealant or sclerosant were injected as a one-stage procedure, into an "unprepared" or infected fistula, this may cause a flare-up of the infection and even further abscess formation.

A gastrointestinal fistula is an abnormal passage that leaks contents of the stomach or the intestine (small or large bowel) to other organs, usually other parts of the intestine or the skin. For example, gastrojejunocolic fistulae include both enterocutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

Treatment options for gastrointestinal fistulae vary. Depending on the clinical situation, patients may require IV nutrition and a period of time without food to allow the fistula time to close on its own. Indeed, nonsurgical therapy may allow spontaneous closure of the fistula, although this can be expected less than 30% of the time according to one estimate. A variable amount of time to allow spontaneous closure of fistulae has been recommended, ranging from 30 days to 6 to 8 weeks. During this preoperative preparation, external control of the fistula drainage prevents skin disruption and provides guidelines for fluid and electrolyte replacement. In some cases, surgery is necessary to remove the segment of intestine involved in a non-healing fistula.

There remain needs for improved and/or alternative medical products, methods, and systems that are useful for treating fistulae. The present invention is addressed to those needs.

SUMMARY

The present invention provides, in certain aspects, unique medical products for treating fistulae having at least a primary opening in the alimentary canal and a fistula tract. Certain embodiments of the invention relate to fistula grafts which are configured to have portions residing in and around a primary fistula opening, such as an anorectal fistula primary opening. For example, some inventive fistula grafts include a biocompatible graft body which is configured to block at least the primary fistula opening, wherein the graft body includes a capping member and an elongate plug member, which extends from the capping member. The capping member is configured to contact portions of the alimentary canal wall adjacent to the primary opening, and the elongate plug member is configured to extend into at least a portion of the fistula tract. The capping member and the elongate plug member may be formed separately and then joined, or alternatively, the two may be formed as a single unit, for example, from a single piece of material. Each of the two members can exhibit any suitable size, shape, and configuration, and in this regard, may be formed with one or more of a variety of suitable biocompatible materials. In some forms, the graft body is configured to seal off or substantially seal off the primary fistula opening when suitably deployed. The capping member and/or the elongate plug member, in certain aspects, comprise an expandable element, for example, an expandable material such as a compressed sponge material and/or an expandable device such as a resilient wire frame. In preferred aspects, the capping member and/or the elongate plug member comprise a remodelable, angiogenic material, for example, a remodelable extracellular matrix material such as submucosa. Further, the medical graft product, in some forms, can include a suture in association with the graft body. This suture can be used, for example, to draw the product into the fistula primary opening and/or secure the product to soft tissues at or near a secondary opening in the fistula.

In one particular embodiment, the invention provides a method for treating a fistula having a primary opening in a wall of the alimentary canal and a fistula tract. This method comprises (i) providing a medical graft product including a biocompatible graft body that is configured to block at least the primary fistula opening, wherein the graft body includes a capping member and an elongate plug member extending from the capping member; and (ii) implanting the medical graft product within a patient so that the capping member contacts portions of the alimentary canal wall adjacent to the primary opening, and the elongate plug member extends into at least a portion of the fistula tract. In certain aspects, a suitably configured medical graft product is implanted so as to seal off or substantially seal off the primary opening. Further, the medical graft product may include an anchoring adaptation useful for maintaining the capping member in contact with portions of the alimentary canal wall adjacent to the primary opening. Suitable anchoring adaptations include but are not limited to adhesives, barbs, hooks, sutures, and the like.

Another embodiment of the present invention provides a medical product, which includes a medical graft product such as that described above enclosed within a sealed package. In certain aspects, this medical product also includes a device suitable for deploying the medical graft product within a patient. Further, the sealed package can include indicia identifying the contents of the package for use in treating a fistula.

In a further embodiment, the present invention provides a medical graft device useful for treating a fistula having at least a primary opening in a bodily structure wall and a fistula tract extending from the primary opening. This medical graft device comprises a biocompatible graft body that includes a capping member and an elongate plug member. The capping member is configured to contact portions of the bodily structure wall adjacent to the primary opening, and includes a support frame supporting a deformable covering material. The elongate plug member extends from the capping member, and is configured to fill at least a portion of the fistula tract. This support frame can be shaped and configured in a variety of manners including some where peripheral portions of the frame lie within a single, generally flat plane. In one aspect, a frame of this sort includes a plurality of sides and bends interconnecting to form a closed circumference frame, wherein the deformable covering material extends between these sides and bends. The covering material may be formed with one or more of a variety of biocompatible materials including some that are naturally derived and some that are non-naturally derived. In some forms, a sheet-form covering material is highly flexible, whether in a single-layer or multi-layer form.

In yet another embodiment of the invention, provided is a method for treating a fistula having at least a primary opening in a bodily structure wall and a fistula tract extending from the primary opening. This method includes providing a medical graft device such as that described directly above, and implanting it within a patient so that the capping member contacts portions of the bodily structure wall adjacent to the primary opening, and the elongate plug member extends into and fills at least a portion of the fistula tract.

In one aspect, the present invention provides a medical graft device useful for treating a fistula having at least a primary opening in a bodily structure wall and a fistula tract extending from the primary opening. This medical graft device comprises a biocompatible graft body that includes a capping member and an elongate plug member. The capping member is collapsible to a collapsed first condition permitting its passage through the fistula tract and the primary opening. In this collapsed first condition, the capping member is expandable to an expanded second condition effective to inhibit its passage back through the primary opening. The elongate plug member extends from the capping member, and is effective to fill at least a portion of the fistula tract. In some forms, the capping member includes a resilient wire support frame, for example, one providing a general two-dimensional or three-dimensional framework when the capping member is in the expanded second condition.

In an additional aspect, the invention provides an apparatus for treating a fistula having at least a primary opening in a bodily structure wall and a fistula tract extending from the primary opening. This apparatus comprises a delivery device configured for passage through the fistula tract and the primary opening, wherein the device has a lumen communicating with a distal end opening. The apparatus further comprise a medical graft device removably positioned in the delivery device lumen. The medical graft device is comprised of a graft body that includes a capping member and an elongate plug member. The capping member is collapsible to a collapsed first condition, which permits the capping member to be positioned in the delivery device lumen for passage through the fistula tract and the primary opening. In this collapsed first condition, the capping member is expandable to an expanded second condition effective to inhibit passage of the capping member back through the primary opening upon its removal from the delivery device lumen. The elongate plug member extends from the capping member, and is effective to fill at least a portion of the fistula tract.

In yet another aspect, the present invention provides a medical graft device useful for treating a fistula having at least a primary opening in a bodily structure wall and a fistula tract extending from the primary opening. This medical graft device comprises an elongate plug body having a proximal portion, a distal portion and a central longitudinal axis. The plug body is configurable from a first condition to a second condition. The first condition permits passage of the plug body distal portion through the fistula tract and the primary opening. The second condition includes the distal portion longitudinally compressed relative to its position in the first plug body condition. When longitudinally compressed in this manner, the distal portion includes peripheral regions extended laterally away from the plug body central longitudinal axis relative to their position in the first plug body condition so as to inhibit passage of the plug body distal portion back through the primary opening. The plug body proximal portion is configured to extend into and fill at least a portion of the fistula tract. The medical graft device further includes an actuating member, which is coupled to the plug body distal portion, and traverses proximally along the plug body to be extendable though the fistula tract. The actuating member is actuatable to convert the plug body from the first condition to the second condition.

In another embodiment of the present invention, provided is a medical graft device useful for treating a fistula having at least a primary opening in a bodily structure wall and a fistula tract extending from the primary opening. This medical graft device comprises a biocompatible graft body that includes a capping member and an elongate plug member. The capping member is collapsible to a collapsed first condition, which permits its passage through the fistula tract and the primary opening. In this collapsed first condition, the capping member is expandable to an expanded second condition, which inhibits its passage back through the primary opening. The elongate plug member extends from the capping member, and is effective to fill at least a portion of the fistula tract. The medical graft device also includes an actuating member, which is connected to the capping member and traverses proximally along the elongate plug member to be extendable through the fistula tract. The actuating member is actuatable to convert the capping member from the collapsed first condition to the expanded second condition.

The present invention also provides, in another embodiment, a medical graft device useful for treating a fistula having at least a primary opening in a bodily structure wall and a fistula tract extending from the primary opening. This medical graft device comprises a biocompatible graft body, which includes a capping member and an actuating member extending from the capping member. The capping member includes a deformable covering material that is deformable to define a convex surface for contacting patient tissue at the primary opening. This convex surface has an externalized material portion and an internalized material portion. The externalized material portion is configured to reside externally of the fistula tract when the graft device is implanted and the covering material is deformed. The internalized material portion is configured to reside within the fistula tract when the graft device is implanted and the covering material is deformed. The actuating member is configured to extend through the fistula tract when the graft device is implanted, and is actuatable to convert the covering material to the deformed condition. The actuating member can exhibit a variety of shapes and configurations. In some forms, the actuating member includes a volumetric plug body that is coupled to a centrally-located region of the deformable covering material.

In a further embodiment, the invention provides a delivery apparatus for delivering a fistula plug into a fistula tract. This apparatus comprises a deployment device having a lumen communicating with a distal end opening. Additionally, this apparatus comprises a fistula plug having a plug body partially received through the distal end opening. This plug body has an internalized plug body portion and an externalized plug body portion, wherein the externalized plug body portion is configured to remain forward of the distal end opening during traversal of the fistula tract.

In yet another embodiment, the invention provides a method of delivering a fistula plug to a fistula tract. This method comprises providing a delivery apparatus such as that described directly above, and forcing this delivery apparatus into a fistula tract such that the distal end opening traverses at least a segment of the tract and the externalized plug body portion remains forward of the distal end opening during this traversal.

In one particular embodiment, the present invention provides a medical product that includes one or more of the medical graft devices described above enclosed within a sealed package.

Other objects, embodiments, forms, features, advantages, aspects, and benefits of the present invention shall become apparent from the detailed description and drawings included herein.

BRIEF DESCRIPTION OF THE DRAWINGS

FIG. 12A is a perspective view of another medical graft device of the invention.

FIG. 12B shows the medical graft device of FIG. 12A implanted within a patient.

DETAILED DESCRIPTION

Figure 1:
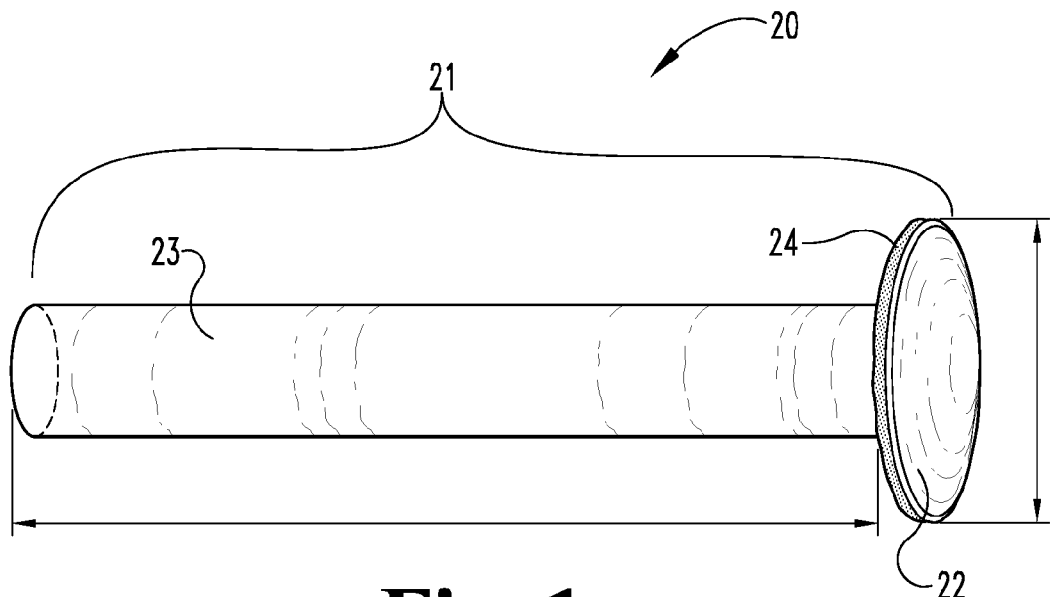
FIG. 1 is a perspective view of an illustrative medical graft product of the invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique medical graft products and methods for treating fistulae including those having at least a primary opening in the alimentary canal and a fistula tract extending from this opening. For example, some inventive graft products include a biocompatible graft body which is configured to block at least the primary fistula opening, wherein the graft body includes a capping member and an elongate plug member extending from the capping member. The capping member is configured to contact portions of the alimentary canal wall adjacent to the primary opening, and the elongate plug member is configured to extend into at least a portion of the fistula tract. The biocompatible graft body preferably comprises a remodelable material, for example, a remodelable extracellular matrix material such as submucosa. The invention also provides methods utilizing such graft products and medical products that include such graft products enclosed within sterile packaging.

The materials used to form the medical graft products of the present invention should generally be biocompatible, and in advantageous embodiments of the products, are comprised of a remodelable material. Particular advantage can be provided by medical products including a remodelable collagenous material. Such remodelable collagenous materials, whether reconstituted or non-reconstituted, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within tissue in which a medical graft product of the invention is implanted, e.g., around tissue defining a fistula tract or an opening to a fistula.

Suitable remodelable materials can be provided by collagenous extracellular matrix (ECM) materials possessing biotropic properties. For example, suitable collagenous materials include ECM materials such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Medical graft products of the invention can include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

ECM materials used in the invention may be free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Turning now to a discussion of drying techniques that can be useful in certain embodiments of the invention, drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described below.

A suitable lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure, that is characteristic of the harvested ECM material.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

In certain aspects, the invention provides medical products including a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the assembly while simultaneously pressing the assembly together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating–at about room temperature (about 25° C.) or with cooling. Relatively low temperature conditions also, of course, include lyophilization conditions.

Medical products of the invention may include biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Suitable biocompatible medical products of the invention can also include a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

Turning now to a discussion of particular medical graft products, systems, and methods of the present invention useful for treating fistulae, illustrative medical graft products of the invention are configured to block at least the primary opening of a fistula, i.e., the primary opening and potentially one or more other segments of a fistula, for example, the fistula tract and/or any secondary openings. In this context, the term "fistula tract" is meant to include, but is not limited to, a void in soft tissues extending from a primary fistula opening, whether blind-ending or leading to one or more secondary fistula openings, for example, to include what are generally described as simple and complex fistulae. Fistula grafts of the invention include a biocompatible graft body including a capping member and an elongate plug member extending from the capping member. The capping member is configured to contact portions of the alimentary canal wall adjacent to the primary opening, and the elongate plug member is configured to extend into at least a portion of the fistula tract. In performing these functions, the capping member and the elongate plug member can exhibit any suitable size and shape and can include any suitable device and/or material, as long as the graft body is able to block at least the primary opening of a fistula, e.g., the primary opening of an anorectal fistula.

The capping member and the elongate plug member may be formed as a single unit (e.g., from a single piece of biocompatible material), or alternatively, the two members may be formed separately and then combined with one another, for example, using an adhesive, by suturing, using mechanical fastener(s), and/or any other suitable joining means. When formed separately, the two may or may not be comprised of the same biocompatible material(s). In certain preferred aspects, the capping member and/or the elongate plug member are comprised of a remodelable material such as a remodelable ECM material. Illustratively, the capping member and the elongate plug member can be formed from separate pieces of remodelable SIS material, and thereafter coupled to one another to form the graft body. However, it should be noted that, in certain aspects, the capping member and the elongate plug member are formed from separate pieces of material, yet are retained in association with one another without the use of any other device or material (e.g., sutures, an adhesive, etc.). In such aspects, the capping member and the elongate plug member are held together by having at least one member (or any portion thereof) received around, through, over, etc., the other member (or any portion thereof).

In some forms, an elongate plug member and a capping member are formed as separate constructs, and then coupled to one another with an absorbable coupling device or material (e.g., an adhesive). Coupling devices can exhibit any suitable size, shape, and configuration, and in some embodiments, take the form of one or more hooks, fasteners, barbs, straps, suture strands, or combinations thereof. Also, such coupling elements may be comprised of one or more of a variety of suitable biocompatible materials exhibiting a rate of degradation upon implantation in vivo, such as but not limited to a 2-0 vicryl suture material. Illustratively, a coupling element can be adapted to desirably hold a capping member and plug member in association with another during product handling and implantation, and then upon implantation, to degrade at a desirable rate. In some modes of operation, the capping member and elongate plug member, at least due in part to degradation of the coupling element, can uncouple or otherwise disengage from one another after a period of time following implantation, allowing the capping member to pass through and out of the bowel with naturally occurring fecal mater. Such decoupling can be facilitated and/or promoted by naturally occurring forces generated during peristalsis.

When implanted in accordance with the present invention, and thus contacting portions of the alimentary canal wall adjacent to the primary opening, the capping member may or may not have a portion extending into the primary opening. For example, in some aspects, the graft body is configured so that no portion of the capping member resides within the primary opening when the graft body is implanted, while in other aspects, the graft body is configured so that a portion of the capping member does reside within the primary opening when the graft body is implanted. Also, it should again be noted that the graft body as a whole, i.e., the combination of the capping member and the elongate plug member, is configured to block at least the primary opening of a fistula. However, neither the capping member portion of the graft body nor the elongate plug member portion of the graft body need be configured to block the primary fistula opening independent of the other member, although either member may be so configured. Additionally, the capping member portion of the graft body, by itself, may or may not be configured to block the fistula tract. In this regard, blocking a particular space or void can be accomplished by filling that space with the capping member, or a portion thereof. In certain aspects, the capping member can be configured to fill the primary opening and/or a portion of the fistula tract. Such filling can, in some embodiments, seal off or substantially seal off the primary opening and/or a portion of the fistula tract.

When suitably implanted, and thus extending into at least a portion of the fistula tract, the elongate plug member may or may not have a portion extending into the primary opening. For example, in some aspects, the graft body is configured so that at least a portion of the elongate plug member resides within the fistula tract but no portion of the elongate plug member resides within the primary opening when the graft is implanted. In other aspects, the elongate plug member is configured to extend through the primary opening and into at least a portion of the fistula tract when the graft body is implanted. Again, it is the graft body as a whole, i.e., the combination of the capping member and the elongate plug member, that is configured to block at least the primary opening of a fistula. Neither the capping member portion of the graft body nor the elongate plug member portion of the graft body need be configured to block the primary opening independent of the other member, although either member may be so configured. Additionally, the elongate plug member portion of the graft body, by itself, may or may not be configured to block the fistula tract. Further, the elongate plug member portion, by itself, may or may not be configured to block any secondary fistula opening. In this regard, blocking a particular space or void can be accomplished by filling that space with the elongate plug member, or a portion thereof. In certain aspects, the elongate plug member can be configured to fill the primary opening, the fistula tract (or any portion thereof), and/or any secondary openings of the fistula. Such filling can, in some embodiments, seal off or substantially seal off the primary opening, the fistula tract (or any portion thereof), and/or any secondary opening of the fistula.

In certain aspects, the medical graft product comprises a material receptive to tissue ingrowth. In such aspects, upon deployment of the product in accordance with the present invention, cells from the patient can infiltrate the material, leading to, for example, new tissue growth on, around, and/or within the medical graft product. In some embodiments, the medical graft product comprises a remodelable material. In these embodiments, the remodelable material promotes and/or facilitates the formation of new tissue, and is capable of being broken down and replaced by new tissue in such a way that the original fistula closure achieved by the implanted graft product is maintained throughout the remodeling process so as to eventually form a closure or substantial closure with the new tissue.

Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any component of a medical graft product of the invention (including any ECM material) can have a level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

In certain aspects, a medical graft product of the invention includes at least two regions exhibiting differing properties, e.g., differing porosities. Such differing regions can be established in certain locations, for example, locations providing a particular arrangement or pattern on and/or within the medical product, and in some forms, such differing regions are formed by subjecting the medical product to a suitable differential drying process. Illustratively, a graft body can be configured so that the capping member occupies a more diminished porosity region, while the elongate plug member occupies a more open porosity region. In this configuration, the diminished matrix region can help isolate the fistula tract from the alimentary canal, thus inhibiting bacteria and other undesirable substances from passing into the alimentary canal from the fistula, while the more open matrix region serves to promote more rapid closure of the fistula with its desirable remodeling properties.

Turning now to a general discussion regarding methods of the invention for treating fistulae, suitable treatment methods include providing a medical graft product such as any of those described above, and implanting the product within a patient so that: (i) the graft body blocks at least the primary opening of a fistula, i.e., the primary opening and potentially one or more other segments of a fistula, for example, the fistula tract and/or any secondary openings; (ii) the capping member contacts portions of the alimentary canal wall adjacent to the primary opening; and (iii) the elongate plug member extends into at least a portion of the fistula tract. Producdts and methods of the invention can be used to treat any fistula, and in particular, fistulae having a primary opening in a wall of the alimentary canal. In some aspects, the invention provides medical graft products and methods useful for blocking openings anywhere on or within the body of a patient, for example, blocking at least the primary opening of a urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, rec to-urethral fistulae, or recto-prostatic fistulae. Also, inventive products and methods can be used to treat a fistula regardless of its size and shape, and in some forms, are utilized to treat a fistula having a primary opening, secondary opening, and/or fistula tract with a diameter ranging from about 1 millimeter to about 20 millimeters, more typically from about 5 millimeters to about 10 millimeters.

Medical products of the invention can be implanted using any suitable delivery method or placement technique. Illustratively, a graft body can be implanted by pulling or pushing the graft body into a suitable position within a fistula. For example, the elongate plug member end of the body can be pulled toward a secondary opening within the fistula tract (e.g., through the primary opening and into the fistula tract) until the capping member contacts portions of the alimentary canal wall adjacent to the primary opening. In certain embodiments, such pulling can be accomplished using a fistula probe or other suitable instrument, for example, an appropriately configured pair of surgical hemostats that include a portion passable into a secondary opening, through the fistula tract, and potentially out of the primary opening. Thereafter, the elongate plug member portion of the graft body can be releasably grasped by the probe or otherwise coupled to the probe and pulled into the primary opening. In other embodiments, an illustrative graft body is suitably deployed using a biocompatible sheath or catheter, which can be configured to traverse the tract of a fistula, and is optionally located within the fistula tract over a suitable wire guide or under endoscopic guidance. In these embodiments, an illustrative graft construct can be deployed in an over-the-wire configuration or through an unobstructed sheath lumen. In addition to those described elsewhere herein, suitable delivery devices and systems useful in such embodiments of the invention can be prepared and used, for example, as described in U.S. Provisional Application Ser. No. 60/763,550 entitled "FISTULA GRAFT DEPLOYMENT SYSTEMS AND METHODS" (Cook Biotech Incorporated) filed on Jan. 31, 2006, which is hereby incorporated by reference in its entirety.

Fistula treatment methods of the invention may include an endoscopic visualization (fistuloscopy) step. Such endoscopic visualization can be used, for example, to determine the shape and size of the fistula, which in turn can be used to select an appropriately sized and shaped medical graft product for treating the fistula. Illustratively, a very thin flexible endoscope can be inserted into a secondary opening of the fistula and advanced under direct vision through the fistula tract and out through the primary opening. By performing fistuloscopy of the fistula, the primary opening can be accurately identified. Also, cleaning of the fistula can be performed prior to and/or during deployment of a medical graft product of the invention. For example, an irrigating fluid can be used to remove any inflammatory or necrotic tissue located within the fistula prior to engrafting the product. In certain embodiments, one or more antibiotics are applied to the medical graft product and/or the soft tissues surrounding the fistula as an extra precaution or means of treating any residual infection within the fistula.

The present invention also provides, in certain aspects, medical devices that include a radiopaque element such as but not limited to a radiopaque coating, attached radiopaque object, or integrated radiopaque substance. In this regard, the capping member and/or elongate plug member of some inventive graft bodies may be comprised of a radiopaque element so that, for example, the movement of the body may be monitored during deployment and the body may be placed at a desirable location. Any suitable radiopaque substance, including but not limited to, tantalum such as tantalum powder, can be incorporated into a medical product of the invention. Other radiopaque materials comprise bismuth, iodine, and barium, as well as other suitable markers.

In some forms, a fistula is drained prior to receiving a medical graft product of the invention therein. Such draining can be accomplished by inserting a narrow diameter rubber drain known as a seton (Greek, "thread") through the fistula. The seton is passed through the fistula tract and tied as a loop around the contained tissue and left for several weeks or months, prior to definitive closure or sealing of the fistula. This procedure is usually performed to drain infection from the area, and to mature the fistula tract prior to a definitive closure procedure.

In one embodiment, a medical graft product of the invention includes a leader in association with the graft body, for example, a suture glued or tied to the graft body. This leader can be used to pull the graft body into a suitable position within a fistula. In some aspects, after the leader is used to sufficiently locate a suitable fistula graft within a patient, the string can be removed from the graft, for example, using cutting shears. In alternative forms, the string or suture can be made from a remodelable or otherwise resorbable material such that the string or suture can be left in place within the fistula tract. In these forms, the resorbable leader can be used to anchor or otherwise suitably secure the fistula graft within the implantation site. For example, the leader can be tied to patient tissue at a suitable location, for example, a location just inside or external to a secondary fistula opening. Further, in alternative embodiments, an illustrative fistula graft can be positioned so that it spans the entire length of a fistula tract, i.e., from the primary opening to a location at or external to a secondary opening. In these embodiments, the string or suture can be used to secure the tail of the graft to patient tissue at an external location.

With reference now to FIG. 1, shown is a perspective view of an illustrative medical graft product 20 of the present invention. The graft product 20 includes a biocompatible graft body 21 that is configured to block at least the primary opening of a fistula. The graft body includes a capping member 22 and an elongate plug member 23, which extends from the capping member 22. The capping member 22, which is formed with an ECM material (e.g., SIS), is generally in the shape of a disk and is configured to contact portions of the alimentary canal wall adjacent to the primary opening. The elongate plug member 23, which is also formed with an ECM material, is generally in the shape of a cylinder and is configured to extend into at least a portion of the fistula tract. It should be noted that the elongate plug member 23 (and any other plug member described herein) may or may not be sized and shaped to fill an entire fistula tract.

The capping member and elongate plug member portions of a graft body of the invention, whether formed separately or together as a single unit, can be constructed in any suitable manner, for example, using any of the processes described herein. In some embodiments, the capping member and/or elongate plug member are formed with a reconstituted or otherwise reassembled ECM material.

In other embodiments, a graft body is formed by folding or rolling, or otherwise overlaying one or more portions of a biocompatible material, such as a biocompatible sheet material. In certain embodiments, the overlaid biocompatible sheet material can be compressed and dried or otherwise bonded into a volumetric shape such that a substantially unitary construct is formed, e.g., in a mold having a shape that is similar to the graft body that is depicted in FIG. 1. Such a substantially unitary graft body can then be placed in a fistula in a manner such that the capping member contacts portions of the alimentary canal wall adjacent to the primary opening, and the elongate plug member extends into at least a portion of the fistula tract (and potentially fills the primary fistula opening, the fistula tract, and/or any secondary fistula openings, or any portions thereof). The cross-sectional area of elongate plug member 23 is generally constant along the length of the plug. Although not depicted in FIG. 1, in some forms, the elongate plug member 23 is configured so that its cross section increases in size moving toward the capping member. Such a configuration can provide a more snug fit of the plug at or near the primary opening upon implantation. In some modes, the elongate plug member has portions that are tapered and/or curvilinear.

In certain aspects, the invention provides biocompatible graft bodies that include an expandable element (e.g., an expandable material and/or device). In this regard, inventive graft bodies may be provided, wherein the capping member, the elongate plug member, or both have the capacity to expand. For example, the capping member and/or the elongate plug member depicted in FIG. 1 can include, for example, a suitable ECM foam or sponge form material. Illustratively, a graft body, or any portion thereof, may comprise a porous, three-dimensionally stable body formed with one or more suitable biocompatible matrix materials. Such biocompatible matrix materials can include naturally-occurring polymers and/or synthetic polymers. More preferred sponge compositions will comprise collagen as a matrix-forming material, either alone or in combination with one or more other matrix forming materials, and particularly preferred sponge compositions will comprise an ECM material such as those discussed elsewhere herein. In general, sponge matrices useful in certain embodiments of the present invention can be formed by providing a liquid solution or suspension of a matrix-forming material, and causing the material to form a porous three-dimensionally stable structure; however, a sponge or foam material can be formed using any suitable formation method, as is known in the art.

For additional information concerning foam or sponge form materials that can be useful in certain embodiments of the present invention, reference can be made, for example, to U.S. Pat. App. Pub. No. 2003/0013989.

In some forms, a compact, stabilized sponge construct is highly expansive when wetted, which can desirably enhance the ability of the graft body to block (and to continue blocking) at least the primary opening of a fistula. In illustrative procedures, a suitable hydrant, such as saline, may be applied or delivered to the graft body after it is suitably located within a patient to enhance the expansion of the body within the fistula tract and/or a fistula opening. Alternatively, or additionally, a bodily fluid of the patient can sufficiently wet the implanted graft body so as to promote the expansion of the body within the fistula.

These compact, stabilized sponge constructs and other expandable graft body elements, when used in the invention, can allow the graft body to attain a more low-profile configuration during a deployment step. For example, an illustrative deployment system can include a graft body, wherein the capping member (and optionally also the elongate plug member) is comprised of an expandable device and/or material such that in a stabilized, compressed first configuration, the graft body can fit within an end of a delivery device (e.g., a probing device, delivery sheath, or other similar instrument), which is sized and configured to traverse a fistula tract. Illustratively, this end of the delivery device can be passed into a secondary opening, through a fistula tract, and out of a primary opening into the alimentary canal. Thereafter, the graft body (or at least the capping member portion of the graft body) can be pushed or otherwise removed from the delivery device in a suitable manner to allow the capping member to attain an expanded second configuration. In such an expanded configuration, the capping member, which was previously able to traverse the primary fistula opening, is now sized and shaped to contact portions of the alimentary canal wall adjacent the primary opening so that at least a portion of the capping member cannot easily pass back through the primary opening.

Figure 2:
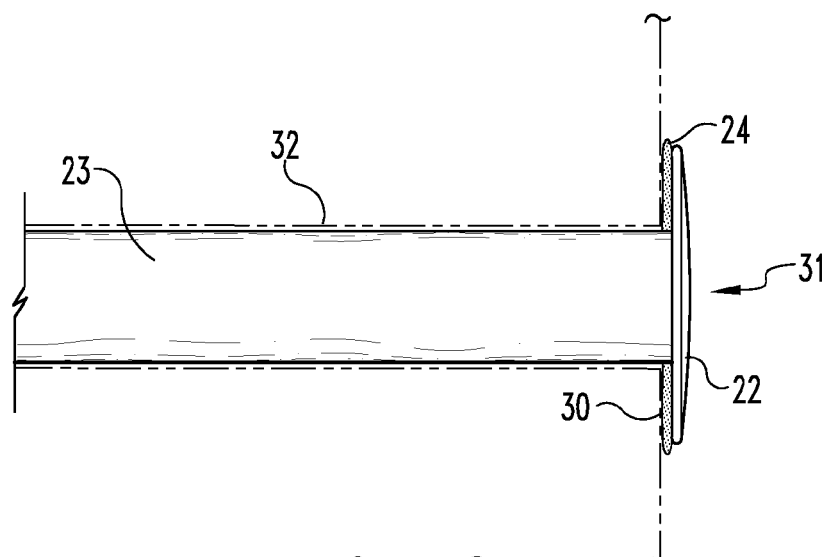
FIG. 2 is a side view of the medical graft product of FIG. 1 implanted within a patient.

FIG. 2 shows an illustrative manner of utilizing graft product 20 to treat a patient. As depicted, graft product 20 can be implanted within a patient so that capping member 22 contacts portions of alimentary canal wall 30 adjacent to primary opening 21, and elongate plug member 23 extends into at least a portion of fistula tract 32. In certain forms of the invention, a graft product incorporates an anchoring adaptation to maintain the capping member in contact with portions of the alimentary canal wall adjacent the primary opening following product implantation. For example and as shown in FIG. 1, the medical product 20 can include an adhesive 24 for maintaining this type of contact. In some but not all aspects, the adhesive separates the capping member from the alimentary canal wall, and in this context, the adhesive may be considered part of the capping member. Adhesive 24 can be applied to the graft product before an implantation procedure, e.g., during manufacture of the product, or alternatively, can be applied to the graft product and/or to tissue at or near the primary opening during such an implantation procedure. Other suitable anchoring adaptations include but are not limited to barbs, hooks, sutures, protuberances, ribs, and the like. Again, such anchoring adaptations, while advantageous in certain forms of the invention, are not necessary to broader aspects of the invention. Illustratively, certain medical graft products are configured so that the capping member is able to maintain contact with portions of the alimentary canal wall adjacent to the primary opening following implantation without the need for such anchoring adaptations. In other aspects, suitable anchoring adaptations aid or facilitate the maintenance of such contact.

Additionally, in illustrative embodiments, one or more anchors, barbs, ribs, protuberances, and/or other suitable surface modifications can be incorporated on and/or within an illustrative graft body to roughen, condition, or otherwise de-epithelialize at least a portion of the fistula, such as the fistula tract and/or the primary opening, during and/or after emplacement of the graft within the tract. The conditioning of the tract tissue can serve to initiate a localized healing response in patient tissue that can be advantageous in enhancing the ingrowth of patient tissue into an illustrative plug construct, such as a plug comprising an ECM material. Further, in illustrative embodiments, where a suture, leader, or string is used to assist with the emplacement of an illustrative graft construct within a tract, as is discussed elsewhere herein, the leader can comprise an abrasive material, or comprise one or more sections and/or surface features and/or adaptations, e.g. one or more bristles that can directionally emanate from the leader material and that can serve to roughen or otherwise condition or de-epithelialize patient tissue upon travel through and/or location within a fistula tract.

In certain aspects, medical graft products of the invention incorporate an adhesive or, where appropriate, a sclerosing agent to facilitate and/or promote blocking of at least the primary opening of the fistula. As well, fistula treatment methods of the invention can include steps where such substances or materials are applied to a medical graft product being deployed and/or to the soft tissues surrounding the fistula. For example, an adhesive, glue or other bonding agent may also be used in achieving a bond between a medical graft product of the invention and the soft tissues defining a fistula opening or tract and/or adjacent tissues. Suitable bonding agents may include, for example, fibrin or collagen gels or pastes, gelatin, or other agents including reactive monomers or polymers, e.g., cyanoacrylate adhesives. In some forms of the invention, a fistula treatment method includes contacting soft tissue surfaces surrounding the fistula, e.g., soft tissue surfaces at or near the primary opening and/or soft tissues lining the fistula tract, with a sclerosing agent prior to forcing the sheet from material into the fistula. Such use of a sclerosing agent can de-epithelialize or otherwise damage or disrupt these soft tissue surfaces, leading to the initiation of a healing response.

Although the capping member 22 depicted in FIG. 1 is formed with an ECM material and is generally in the shape of a disk, capping members of the invention can have any suitable size, shape, and configuration, and can include any suitable device and/or material for contacting portions of the alimentary canal wall adjacent to the primary opening. Illustratively, the capping member can include one or more objects (e.g., pieces of material) that, together or alone, exhibit a three-dimensional rectilinear or curvilinear shape. Suitable three-dimensional rectilinear shapes can have any suitable number of sides, and can include, for example, cubes, cuboids, tetrahedrons, prisms, pyramids, wedges, and variations thereof, just to name a few. Suitable three-dimensional curvilinear bodies can include, for example, spheres, spheroids, ellipsoids, cylinders, cones, and any suitable variations thereof (e.g., a segment of a sphere, or a truncated cone, etc.), just to name a few.

Figure 3:
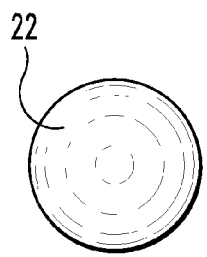
FIG. 3 is a perspective view of an illustrative capping member of the invention.

With reference now to FIG. 3, shown is an alternative capping member 22, which is generally in the shape of a bead. This illustrative capping member can be coupled to or otherwise joined with any of the elongate plug members described herein (e.g., the plug member depicted in FIGS. 5 and 6, as two non-limiting examples). This capping member is comprised of an absorbable material, and is generally sized and adapted to suitably contact portions of the alimentary canal wall adjacent to a primary fistula opening. In some forms, such a capping member comprises an expandable sponge material, e.g., any of those described above. In these forms, the capping member can fit through a primary fistula opening in a first, compressed configuration; however, in a second, expanded configuration, the member cannot cleanly fit back through the same opening and can be wedged into the opening.

Figure 4A:
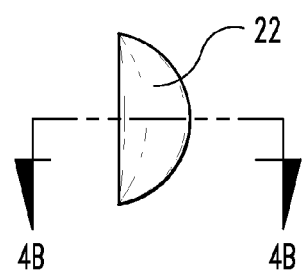
FIG. 4A is a side view of another illustrative capping member of the invention.
Figure 4B:
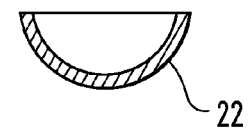
FIG. 4B is a cross section view of the capping member of FIG. 4A along the view line 4-4 shown in FIG. 4A.

FIG. 4A shows a side view of another alternative capping member 22 of the present invention. This particular capping member generally exhibits the shape of a lens or bowl. Such a bowl- or lens-shaped capping member may or may not have a hollow portion. This capping member can be coupled to or otherwise joined with any of the elongate plug members described herein, and the two members can be joined in any suitable manner and in any suitable configuration relative to one another, for example, so that peripheral regions of either the top or bottom face of the lens contacts portions of the alimentary canal wall adjacent to the primary opening. (FIG. 4B provides a cross section view of the capping member of FIG. 4A along the view line 4-4 shown in FIG. 4A).

Figure 5:
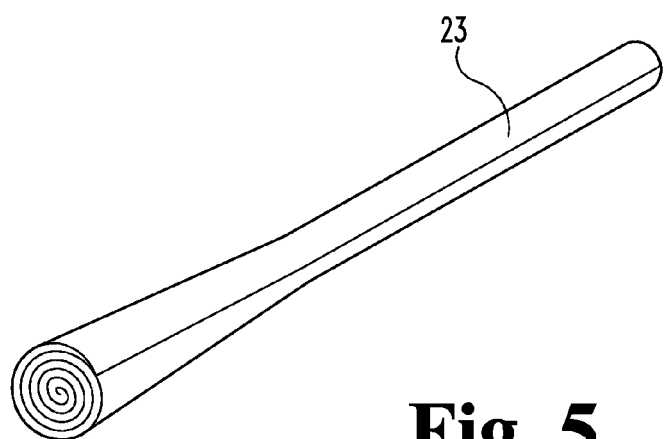
FIG. 5 is a perspective view of an illustrative elongate plug member of the invention.

With reference now to FIG. 5, shown is an illustrative elongate plug member 23 of the invention exhibiting a truncated, generally conical shape. This elongate plug member includes a layered volumetric graft construct including, for example, a rolled remodelable material that occupies a substantially unitary volume. The elongate plug member can be coupled to or otherwise joined with any of the capping members described herein, for example, the disk-shaped capping member of FIG. 1 or the bead-shaped capping member of FIG. 3, just to name a few. Such an elongate plug member can be prepared, for example, as described in U.S. patent application Ser. No. 11/415,403, titled "VOLUMETRIC GRAFTS FOR TREATMENT OF FISTULAE AND RELATED METHODS AND SYSTEMS" (Cook Biotech Incorporated) filed May 1, 2006, which is hereby incorporated by reference in its entirety.

Illustratively, such a plug member can be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, such a plug member is formed by randomly or regularly packing one or more pieces of single or multilayer ECM sheet material within a mold and thereafter processing the packed material.

Illustrative elongate plug members of the invention will be of sufficient size and shape to extend into at least a portion of a fistula tract, and will generally (but not necessarily) be of sufficient dimension to fill a fistula, or a segment thereof, e.g., the primary fistula opening, a fistula tract, and/or any secondary fistula openings, either alone or in combination with other similar or differing devices. In certain embodiments, the elongate plug member will have a length of at least about 0.20 cm, and in many situations at least about 1 cm to about 20 cm (approximately 1 to 8 inches). In illustrative embodiments, the plug member will have a length of from about 2 cm to about 5 cm, or alternatively, from about 2 inches to about 4 inches. Additionally, in certain embodiments, elongate plug members will have a diameter, which may or may not be constant along their length, of from about 0.1 mm to about 25 mm, or more typically from about 5 mm to about 10 mm. In certain embodiments, a generally conical plug member is tapered along its length so that the end of the plug member proximate the capping member has a diameter of about 5 mm to about 10 mm and the opposite end of the plug member has a diameter of about 0.5 mm to about 3 mm. Such a taper may or may not be continuous along the length of the elongate plug member.

Figure 6:
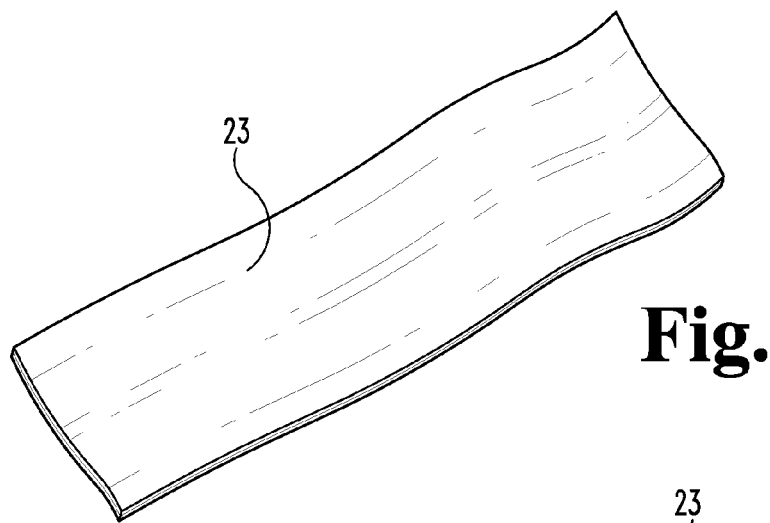
FIG. 6 is a perspective view of another illustrative elongate plug member of the invention.

With reference now to FIG. 6, shown is a perspective view of another illustrative elongate plug member of the invention. The elongate plug member comprises a compliant sheet form biocompatible material comprising two layers of ECM material bonded together. This sheet form elongate plug member can be coupled to or otherwise joined with any of the capping members described herein, for example, the disk-shaped capping member of FIG. 1 or the bead-shaped capping member of FIG. 3, just to name a few. This sheet form plug member can be prepared, for example, as described in U.S. patent application Ser. No. 11/414,682, titled "FISTULA GRAFT WITH DEFORMABLE SHEET-FORM MATERIAL" (Cook Biotech Incorporated) filed Apr. 28, 2006, which is hereby incorporated by reference in its entirety.

The sheet form material is deformable upon impingement by soft tissue surrounding a fistula (e.g., tissue surrounding the primary fistula opening, the fistula tract, and/or any secondary fistula openings). Such deformable materials can include any of the ECM or other biocompatible materials described herein, for example, a multilaminate sheet of remodelable SIS material. Further, the sheet form plug is sized and shaped so as to be deformable to a three-dimensional volumetric body extending into at least a portion of the fistula tract, and potentially filling at least a portion of the fistula tract, the primary opening, and/or any secondary openings of the fistula. In so doing, advantageous implant materials will also be sufficiently flaccid to avoid substantial cutting or tearing of the surrounding soft tissues.

The sheet form elongate plug member can have any suitable size and shape to treat a fistula having a primary opening in the alimentary tract of a vertebrate, especially a human. In general, the size and shape of the sheet form biocompatible material selected for a particular treatment application will be based, at least in part, on the general size and shape of the fistula being treated. Further, although the sheet form material depicted in FIG. 1 is generally in shape of a rectangle, elongate plug members of the invention, in certain aspects, can include sheet form material exhibiting any suitable rectilinear or curvilinear shape, for example, an isosceles triangle or any other suitable triangular or triangular-like shape, just to give a few non-limiting examples.)

In certain aspects, a sheet form graft body is shaped and sized such that the diameter of the primary opening is less than the width of the sheet so that as the sheet of material is drawn into the fistula tract, it is forced to fold and/or roll over itself one or more times to conform to soft tissues surrounding the fistula, and is gradually "wedged" into the primary opening, and potentially at least a portion of the fistula tract and/or any secondary openings of the fistula, so as to block these spaces when sufficiently pulled therethrough. Such lodging in place may be sufficient to obviate the need for otherwise securing the graft to the soft tissues at or near the primary opening, fistula tract, and/or any secondary openings. Nonetheless, in certain aspects, the graft is further secured to such soft tissues, for example, by suturing.

Figures 7A, 7B:
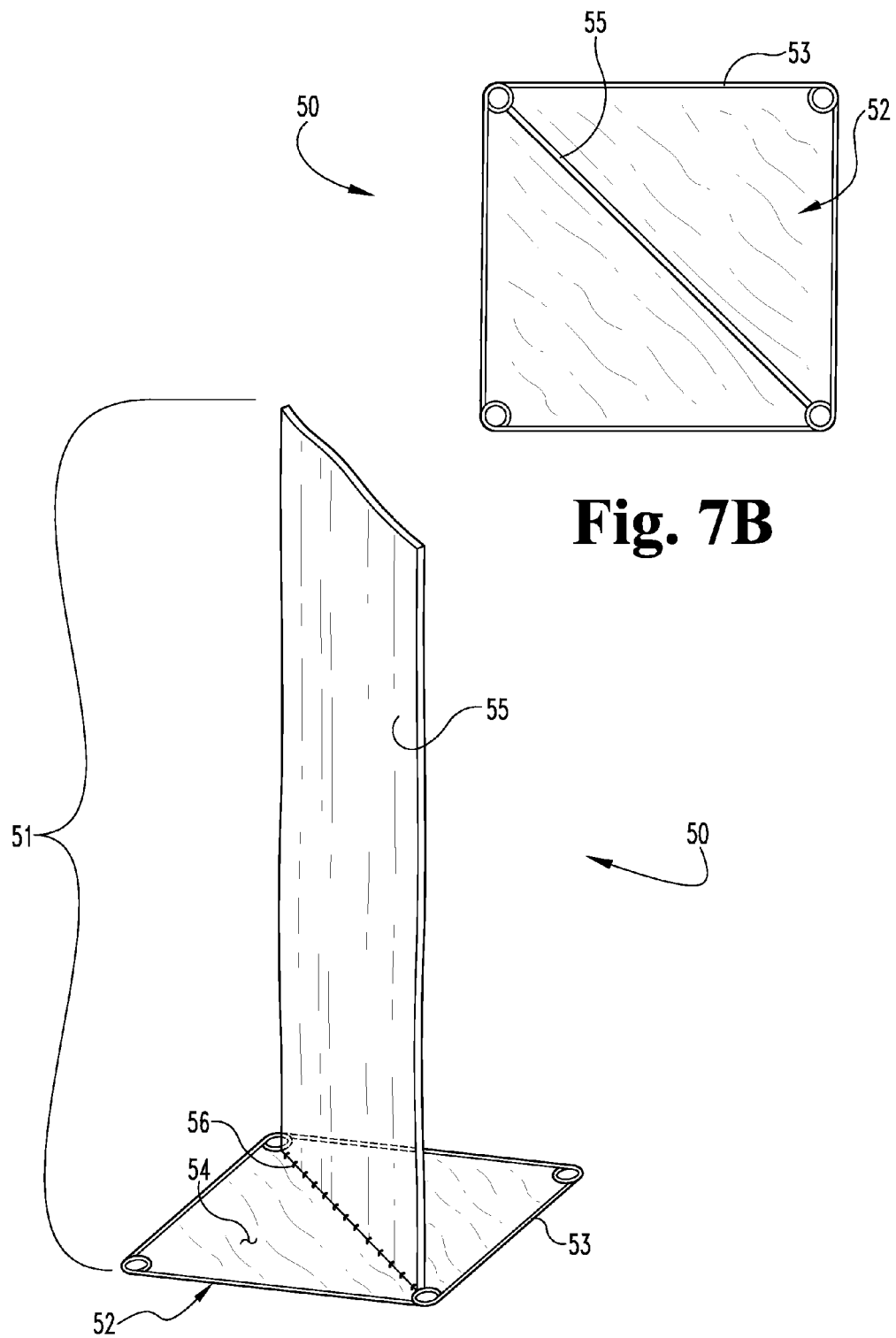
FIG. 7A is a perspective view of another illustrative medical graft product of the invention.
FIG. 7B is a top view of the medical graft product of FIG. 7A.

As previously mentioned, a capping member of the invention may include an expandable element (e.g., an expandable material and/or device). With reference now to FIG. 7A, shown is an illustrative medical graft product 50 of the invention that includes such an expandable capping member. The medical graft product comprises a biocompatible graft body 51 that is configured to block at least the primary opening of a fistula. The graft body includes a capping member 52 and an elongate plug member 55, which extends from the capping member 52. FIG. 7B shows a top view of medical graft product 50.

The elongate plug member 55 is formed with a compliant sheet form material, e.g., a remodelable ECM material, and is attached to the capping member with sutures 56, although other suitable attachment means are contemplated. The plug member is configured to extend into at least a portion of the fistula tract. The capping member 52 is configured to contact portions of the alimentary canal wall adjacent to the primary opening. The capping member 52 includes a frame 53 comprising a single piece of superelastic wire or other material having a plurality of sides and bends interconnecting adjacent sides. The bends can be coils, fillets, or other configurations to reduce stress and fatigue. The single piece of wire is preferably joined by an attachment mechanism, such as a piece of cannula and solder, to form a closed circumference frame.

The frame 53 can comprise a metallic material including but not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, suitable frames can include material in the form of yarns, fibers, and/or resins, e.g., monofilament yarns, high tenacity polyester, and the like. A frame element can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon. Such metallic and other materials may be used in forming other expandable and non-expandable graft body components useful in the present invention. The capping member also includes a flexible material covering 54 extending between sides of the frame 53. Such a covering can be formed with any suitable material such as but not limited to DACRON, PTFE, collagen, submucosa, or other flexible material, and can be attached to the frame 53 with sutures or other suitable attachment means.

Figure 7C:
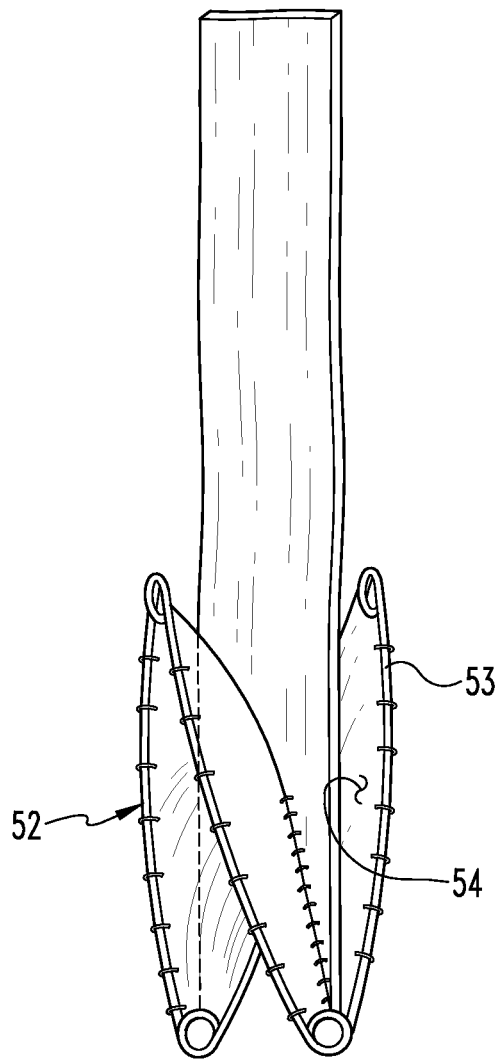
FIG. 7C is a side view of the medical graft product of FIG. 7A in a partially compacted configuration.
Figure 7D:
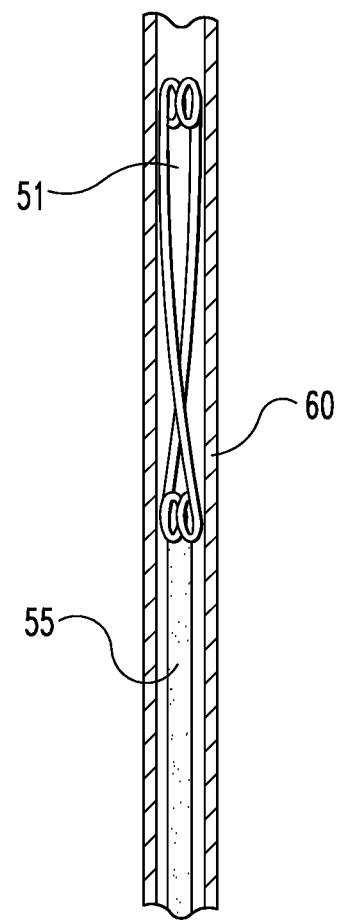
FIG. 7D is a side view of the medical graft product of FIG. 7A in a compacted configuration and received within a lumen of a deployment device.

The capping member 52 has a first configuration wherein the sides and bends generally lie within a single, flat plane as shown in FIGS. 7A and 7B. As shown in FIG. 7C, the member, having four equal sides, can be folded into a second configuration where opposite bends are brought in closer proximity to one another toward one end of the member, while the other opposite ends are folded in closer proximity together toward the opposite end of the member. In the second configuration, the capping member 52 becomes a self-expanding device. In a third configuration and referring now to FIG. 7D, the capping member is compressed into a delivery device 60, such as a catheter, such that the sides are generally beside one another. While the preferred embodiment is four-sided, other polygonal shapes can be used as well. Further, one or more barbs can be attached to the frame 53 for anchoring the device within the patient. The barbs can be extensions of the single piece of wire or other material comprising the capping member frame, or they can represent a second piece of material that is separately attached to the frame by a separate attachment mechanism.

In some modes of operation, the distal end of the deployment device 60 can be inserted into a fistula, for example, into a secondary opening, through a fistula tract, and a distance out of the primary opening. Thereafter, the graft body 50 (or at least the capping member 52) can be removed from the device, for example with a push rod or other suitable device, allowing the capping member 52 to expand as shown in FIGS. 7A and 7B. Then, the graft 50 can be pulled back through the fistula tract until the capping member 52 contacts portions of the alimentary canal wall adjacent to the primary opening. In certain preferred aspects, the cover 54 blocks or facilitates blockage of the primary opening. The delivery device can then be withdrawn from the fistula through the secondary opening, leaving the deformed sheet-form material deployed within at least a portion of the fistula tract, and potentially filling at least a portion of the fistula tract, the primary opening, and/or any secondary openings of the fistula.

Figure 8:
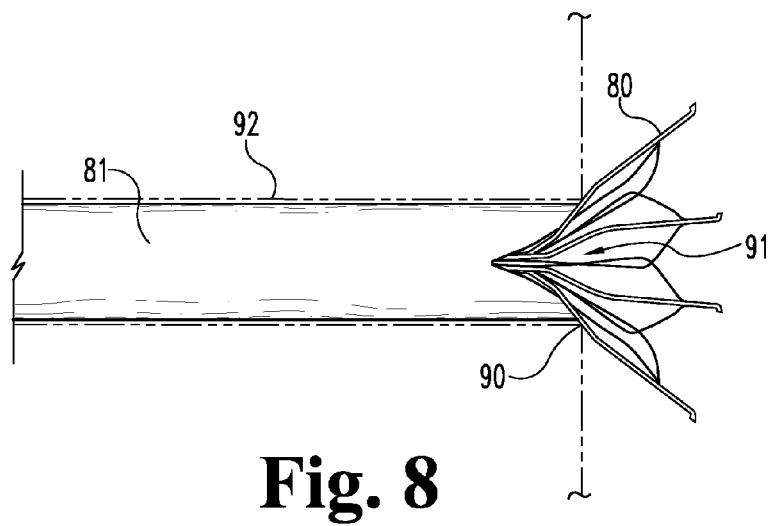
FIG. 8 is a side view of another illustrative medical graft product of the invention implanted within a patient.

FIG. 8 depicts another illustrative medical graft product of the invention implanted within a patient. The graft product includes a biocompatible graft body that is configured to block at least the primary opening of a fistula. The graft body includes a capping member 80 and an elongate plug member 81, which extends from the capping member 80. The elongate plug member 81 is formed with a tube of remodelable material, and is attached to the capping member 80 with glue, although other suitable attachment means, such as but not limited to suturing together with resorbable suture material, are contemplated. The plug member 81 is configured to extend into at least a portion of the fistula tract, and to contact portions of the alimentary canal wall 90 adjacent to the primary opening 91 as shown in FIG. 8. The capping member 81 is comprised of a frame in the form of a tulip filter. Although not shown in the current illustration, the capping member 80 also includes a flexible material covering attached to the tulip filter frame. Such a covering can be formed with any suitable material such as but not limited to DACRON, PTFE, collagen, submucosa, or other flexible material, and can be attached to the tulip filter 80 with sutures or other suitable means. In certain other aspects, such a covering is not included as part of the capping member.

The capping member 80 has a first configuration wherein the opposite sides of the tulip filter are brought in closer proximity to one another so as to be able to fit within the lumen of a delivery device, such as a catheter. In certain aspects, the distal end of the deployment device can be inserted into a fistula, for example, into a secondary opening, through a fistula tract, and a distance out of the primary opening. Thereafter, the graft body (or at least the capping member 80) can be removed from the device, allowing the capping member 80 to expand as shown in FIG. 8. Then, the graft can be pulled back through the fistula tract until the capping member 80 contacts portions of the alimentary canal wall 90 adjacent to the primary opening 91 as shown in FIG. 8. The delivery device can then be withdrawn from the fistula through the secondary opening, leaving the graft deployed within the fistula and blocking at least the primary fistula opening.

Figure 9:
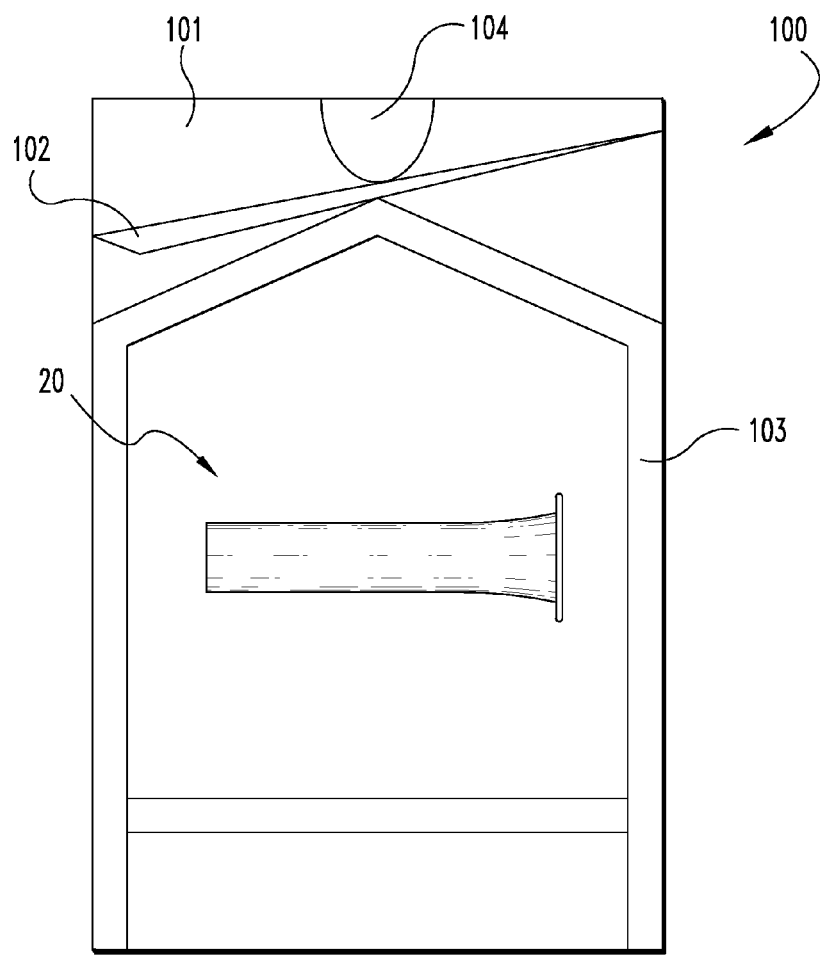
FIG. 9 is a top view of an illustrative medical product of the invention.

With reference now to FIG. 9, shown is a top view of an illustrative medical product 100 of the present invention that includes medical graft product 60 sealed within sterile medical packaging. In particular, medical product 100 has packaging including a backing layer 101 and a front film layer 102 (shown partially drawn away from backing layer 101). The medical graft product is sealed between backing layer 101 and film 102 utilizing a boundary of pressure-adhesive 103 as is conventional in medical packaging. A cut-out 104 may be provided in the backing layer 101 to assist a user in separating the film layer 102 from the backing layer 101.

Sterilization of the medical product 100 may be achieved, for example, by irradiation, ethylene oxide gas, or any other suitable sterilization technique, and the materials and other properties of the medical packaging will be selected accordingly. Also, medical graft products of the invention can be contained in sterile packaging in any suitable state. Suitable states include, for example, a hydrated or dehydrated state. The medical graft products can be dehydrated by any means known in the art (e.g., lyophilization or air dried). If a medical graft product of the present invention is stored in a dehydrated state, it is preferred that it retains all of its biological and mechanical properties (e.g., shape, density, flexibility, etc.) upon rehydration.

The materials and other properties of the packaging will be selected accordingly. For example, the package can include indicia to communicate the contents of the package to a person and/or a machine, computer, or other electronic device. Such indicia may include the dimensions of, the type of materials used to form, and/or the physical state of, the contents of the package. In certain embodiments, a medical graft product is packaged for sale with instructions for use. For example, in a particularly preferred embodiment, a medical product includes at least one medical graft product sealed within a sterile package, wherein the packaging has visible indicia identifying the at least one medical graft product as having physical characteristics as described herein, and/or can contain or otherwise be associated with printed materials identifying the contents as having such physical characteristics and including information concerning its use as a medical graft product for treating fistulae. The packaging can also include visible indicia relating to the dimension of the at least medical graft product, and/or relating to the treatment site(s) for which the at least one medical graft product is configured.

The present invention also provides a line of medical products, wherein a medical product of the invention includes one or more medical graft products such as those described herein enclosed within a sealed package. When the medical product includes more than one medical graft product, for example, a plurality of medical graft products, the products can each be of substantially the same size and shape, or, alternatively, can vary with respect to size and shape.

Figure 10A:
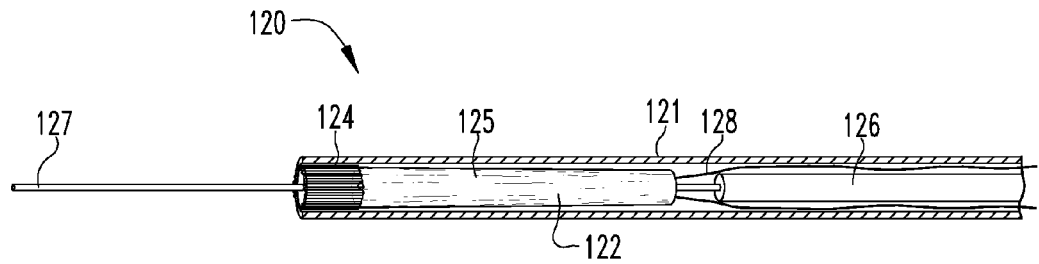
FIG. 10A is a perspective view of a delivery apparatus of the invention received over an emplaced guidewire, the apparatus including a deployment device and a fistula plug.

Fistula plugs of the invention can be adapted for deployment over emplaced wire guides and the like. With reference now to FIGS. 10A through 11B together, shown are two illustrative delivery apparatuses of the invention that include such fistula plugs. While useful in blocking openings anywhere on or within the body of a patient, these apparatuses find particular use in treating entero-enteral or entercutaneous fistulae. FIG. 10A shows one delivery apparatus embodiment 120 of the present invention that includes a cannulated deployment device 121 and a fistula plug 122. Deployment device 121 can exhibit any suitable size, shape and configuration for traversing at least a portion of a fistula, and in some forms, will have an outside diameter approximating the general diameter of the fistula tract through which it passes during a deployment procedure. A delivery device of this sort can be formed with a variety of materials as described elsewhere herein, and in some embodiments, will have a flexibility. Fistula plug 122 comprises a biocompatible plug body 123, at least a portion of which is configured for placement in a fistula, and in some forms, to also block at least the primary opening of a fistula. Plug body 123 includes an expandable, wire-framed capping member 124 and an elongate plug member 125, which extends from and is attached to capping member 124, e.g., using an absorbable suture material.

The elongate plug member 125 is formed with an ECM material, and its cross section increases in size moving toward the capping member 124 to provide a generally tapered plug member that can extend into and fill at least a portion of a fistula tract. The plug member 125 is sized and adapted to be receivable within deployment device 121 as generally shown. The capping member 124 can move between a collapsed or compacted, first position and a expanded, second position, so that upon self-expanding during a delivery step, it can be positioned to contact portions of the alimentary canal wall adjacent to the primary opening. When sufficiently compacted (as shown in FIG. 10A), the capping member 124 can be received within deployment device 121, and has a diameter roughly equal to that of the plug member end to which it is attached. When expanded, capping member 124 is generally disc-shaped, and includes a perimeter frame member and a plurality of interconnected, interior frame members. This and a variety of other frame shapes and configurations will be recognized by those skilled in the art, and are therefore encompassed by the present invention.

Wire-framed capping member 124 may be formed with a metallic material or one or more other suitable materials such as any of those described herein. Although not shown in the current embodiment, the capping member 124 can also include a flexible material covering attached thereto. Nonetheless, it will be understood that, in other aspects, the present invention provides fistula plugs similar to that shown in FIG. 10A except that the capping member does not include an expandable wire frame. These capping members may be any of the capping members described elsewhere herein, and thus, may be considered expandable or non-expandable. For example, such a fistula plug can have an expandable disk or disk-like capping member formed with a synthetic polymeric material (e.g., Nylon), a naturally-derived material (e.g., a collagenous ECM material) or any other suitable material or combination of materials.

Figure 10B:
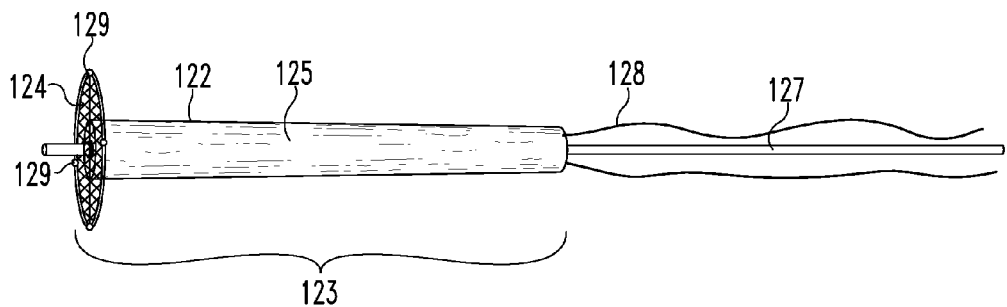
FIG. 10B is a perspective view of the fistula plug and guidewire of FIG. 10A.

Delivery apparatus 120 also includes a pusher device 126, which is slidably receivable within cannulated deployment device 121. Pusher device 126 and plug body 123 are adapted to slide over guide wire 127 as generally shown. In some modes of operation, the distal end of deployment device 121 can be inserted into a fistula over an emplaced guide wire, for example, into a secondary opening, through a fistula tract, and a distance out of the primary opening. Thereafter, the pusher device 126 can be used to push plug body 123 (or at least the capping member 124) from the distal end of device 121, allowing the capping member 124 to expand into a disk or disk-like configuration as shown in FIG. 10B. If not already in a suitable position upon expansion of capping member 124, the plug body 123 can be pulled back through the fistula tract until capping member 124 contacts portions of the alimentary canal wall adjacent to the primary opening, leaving the elongate plug member 125 deployed within and filling at least a portion of the fistula tract. In an alternative embodiment, a delivery apparatus similar to apparatus 120 is provided expect that it is not adapted for use in conjunction with a wire guide.

Pulling in this manner can occur before, after, or while withdrawing deployment device 121 from the secondary fistula opening, and in some modes, is accomplished or at least facilitated by pulling the plug body 123 with anchoring sutures 128. These sutures are coupled to or otherwise associated with plug body 123, and at least provide means for adjusting plug body positioning during and/or after deployment, and potentially also provide means for anchoring the plug body 123 during a deployment step, for example, by being secured to tissue at or adjacent to a secondary fistula opening. Such anchoring can prevent or at least inhibit undesirable migration of plug body 123 for a period of time following deployment. Capping member 124 includes radio-paque elements 129 along its expanded perimeter which can serve as markers (e.g., under fluoro imaging) for confirming desirable placement of plug body 123 at a treatment site.

In some embodiments, an inventive fistula plug includes a capping member (such as any of those described herein) and an elongate plug body having a lumen, wherein the capping member is initially detached from the elongate plug body, but is held in association with the plug body by one or more resorbable sutures that are passed through and/or around the capping member and through the plug body lumen (or alternatively, coupled to the capping member and passed through the plug body lumen). In some forms, such a product includes two or more capping members associated with a plug body (e.g., one occurring at one end of a plug to be positioned at or near a primary fistula opening and one occurring at the opposite plug end to be positioned at or near a secondary fistula opening), wherein any of these capping members may or may not be somehow expandable.

The invention also provides, in certain aspects, apparatuses for delivering a fistula plug to a fistula tract that are comprised of an elongate deployment device having a deployment device distal end; and a fistula plug engaged by the deployment device and having a fistula plug portion extending forward of the deployment device distal end. In some forms, such apparatuses will be configured so that most, if not all, of this fistula plug portion is able to remain forward of the deployment device distal end as this distal end traverses a fistula tract (e.g., is forced into a secondary opening and through at least a segment of a fistula tract). Such apparatuses may or may not be adapted for delivery over an emplaced wire guide or other similar device. The fistula plug and the deployment device can be engaged or otherwise associated with one another in a variety of fashions, and each object can exhibit any suitable size, shape and configuration, to allow the fistula plug and the deployment device to maintain such a relationship while traversing a fistula tract. It will be understood that such fistula plug-deployment device arrangements may or may not involve the fistula plug being attached to the deployment device in some manner. In some cases, a fistula plug is lodged within a deployment device so as to be held there essentially by friction. Additionally or alternatively, a fistula plug may be releasably held (e.g., grasped) by a device.

Illustratively, certain inventive apparatuses are comprised of: (i) a deployment device having a lumen communicating with a distal end opening; and (ii) a fistula plug having a plug body partially received through the distal end opening. This plug body can have an internalized plug body portion and an externalized plug body portion, wherein the externalized plug body portion is configured to remain forward of the distal end opening during traversal of a fistula tract. In some forms, such an internalized plug body portion makes up all but a relatively small portion of the overall plug body, and the externalized portion is able to remain forward of the deployment device distal end opening during a deployment procedure, for example, even when slight to moderate forces act to force the externalized portion into the deployment device lumen during traversal of a fistula tract.

In some modes of operation, such a delivery apparatus is forced into a fistula tract such that the distal end opening traverses at least a segment of the fistula tract and the externalized plug body portion remains forward of the distal end opening during this traversal. For example, the distal end of the deployment device (with the externalized plug body portion extending therefrom) can be passed through a secondary fistula opening and at least partially through a fistula tract (e.g., to a point just shy of the primary fistula opening or through the primary opening). In this context, as the deployment device distal end advances in the fistula tract, the fistula plug also advances in the tract, with at least a portion of the externalized plug body portion remaining outside of the deployment device lumen (and out in front of the deployment device distal end), even as the externalized plug body portion is contacted by patient tissue at the treatment site (e.g., tissue defining the fistula tract).

Although not necessary to broader aspects of the invention, in some embodiments, inventive apparatuses are configured so that an externalized plug body portion makes up about 1% to about 40% of a fistula plug body (by volume), and an internalized plug body portion forms the remainder of the plug body. Illustratively, some inventive apparatuses are configured so that an externalized plug body portion makes up about 1% to about 30% of a fistula plug body (by volume), and in some aspects, about 5% to about 25% of a plug body, and in other aspects, about 5% to about 20% of a plug body (with an internalized plug body portion forming the remainder of the plug body in each of these respective embodiments). Although a plug body-deployment device combination may be configured so that some of the externalized plug body portion will be forced into the deployment device lumen as the deployment device distal end is forced through a fistula tract, in general, inventive apparatuses of this sort will be configured so that substantially all of the externalized plug body portion remains external of the deployment device lumen during a delivery procedure.

Achieving such a plug body-deployment device fit (i.e., wherein all but a relatively small portion of the plug body is received within the deployment device lumen) can be accomplished in a variety of manners, e.g., by experimenting with a variety of plug body and deployment device shapes, sizes, and material(s) of construction. In general, the cross-sectional area of the externalized plug body portion will be greater than the cross-sectional area of the deployment device distal end opening (even in instances where a particular plug body is or becomes, e.g., by hydration, quite flaccid before and/or during delivery). In this context, while the positioning of the externalized plug body portion relative to the deployment device distal end opening may change as the two are at least partially passed through a fistula tract, at least a portion of the externalized plug body portion should remain outside of the deployment device lumen (and extending from the deployment device distal end) during such a procedure.

Figure 11A:
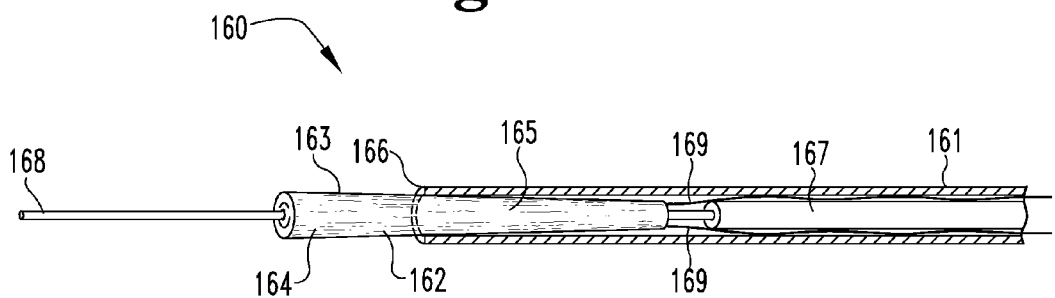
FIG. 11A is a perspective view of another delivery apparatus of the invention received over an emplaced guidewire, the apparatus including a deployment device and a fistula plug.

With reference now to FIG. 11A, shown is another illustrative delivery apparatus 160 of the present invention. Delivery apparatus 160 includes a deployment device 161 and a fistula plug 162. Fistula plug 162 comprises a biocompatible plug body 163 that is configured for deployment in a fistula tract, for example, to lodge within and fill at least a portion of a fistula tract, and in some forms, to block a primary fistula opening. Plug body 163 has an externalized plug body portion 164 and an internalized plug body portion 165. While plug body 163 is a single-piece construct, in an alternative embodiment, a similarly configured plug body includes separately formed externalized and internalized plug body portions that are attached to one another, e.g., using an absorbable suture material. For example, any of the capping members described herein could provide a suitable externalized plug body portion, and any of the elongate plug bodies described herein could provide a suitable internalized plug body portion.

Plug body 163 is formed with an ECM material, and its cross section slightly increases in size moving from internalized plug body portion 165 toward externalized plug body portion 164 to provide a generally tapered plug that can extend into and fill at least a portion of a fistula tract. The dimensions of the externalized plug body portion 164 and internalized plug body portion 165 relative to one another (and relative to the dimensions of a particular deployment device and its lumen) can vary. Generally, plug body 163 is sized and adapted so that when loaded into deployment device 161, externalized plug body portion 164 resides outside of the lumen of deployment device 161 and internalized plug body portion 165 extends into this lumen, even when slight to moderate forces act to force externalized plug body portion 164 into the lumen (e.g., forces encountered while being forced through a fistula tract). Such a plug body-deployment device fit can be accomplished, for example, by providing a tapered plug that, at the point where the externalized plug body portion and the internalized plug body portion meet, has a cross-sectional area approximating the cross-sectional area of the deployment device distal end opening 166. Delivery apparatus 160 also includes an optional pusher device 167, which is slidably receivable within deployment device 161. Although not necessary to broader aspects of the invention, pusher device 167 and plug body 163 can be adapted to slide over a guide wire 168 as generally shown. In some embodiments, a delivery apparatus similar to system 160 is effectively used without an emplaced guidewire, pusher device or both.

In some modes of use, the deployment device distal end opening 166 (with externalized plug body portion 164 extending therefrom) is inserted into a fistula over emplaced guide wire 168, for example, into a secondary opening and at least partially through a fistula tract. With this illustrative configuration, the externalized plug body portion 164 can be advanced to (and potentially through) the primary opening without having to advance the deployment device distal end opening an equal distance through the tract. Also, because externalized plug body portion 164 extends from the distal end of deployment device 161 as the two are advanced through the fistula, the externalized plug body portion 164 can act as a buffer between the deployment device distal end and patient tissue defining the fistula, which can mitigate any damage that might be caused by parts of the deployment device contacting this tissue.

Figure 11B:
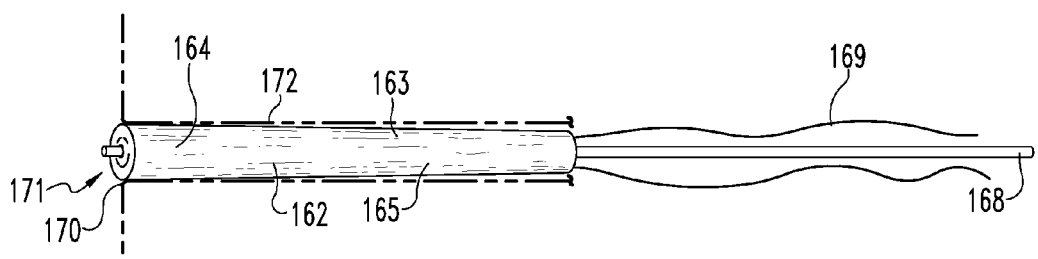
FIG. 11B is a perspective view of the fistula plug and guidewire of FIG. 11A deployed in a fistula tract.

At any suitable point during delivery, pusher device 167 can be used to push plug body 163 from the deployment device distal end opening 166. If not already in a suitable position upon being removed from deployment device 161, the plug body 163 can be subsequently adjusted (e.g., pushed forward or pulled back through the fistula tract) as desired. As shown in FIG. 11B, plug body 163 can be sized and adapted so that when suitably deployed, externalized plug body portion 164, or a portion thereof, is lodged within primary fistula opening 171, and internalized plug body portion 165 extends into and fills at least a portion of a fistula tract 172. In some cases, some of externalized plug body portion will contact portions of an alimentary canal wall 170 adjacent to a primary fistula opening 171. Fistula plug 162 incorporates optional sutures 169 and optional radio-paque element 170.

The present invention also provides, in certain embodiments, graft devices having components that can be caused or allowed to collapse or otherwise have portions extendable away (e.g., radially) from a central longitudinal region to provide a suitable capping arrangement. Such components can be formed separately from, and then suitably united with, the remainder of the graft device, or alternatively, can be formed as part of an existing graft device. In some forms, an elongate plug body has a distal portion configurable from a first condition to a second condition, wherein the first condition permits passage of the plug body distal portion through a fistula tract and out of a fistula opening, and the second condition inhibits passage of the plug body distal portion back through the fistula opening. This second condition can include, in some aspects, one or more parts of the distal end portion laterally extended away from a central longitudinal region of the plug body.

Referring now to FIGS. 12A and 12B, shown is another medical graft device 200 in accordance with the present invention. Graft device 200 includes an elongate plug body 201 having a distal portion 202 and a proximal portion 203. A void 204 extends through a section of distal portion 202 to provide a compressible cap-forming portion 205. Graft device 200 also includes a disc-shaped member 206, which is positioned on the end of distal portion 202. There is a small hole in disc-shaped member 206 through which suture material 207 is passed. Suture material 207 is also passed through a central passage which extends longitudinally through graft body 201. Prior to deployment, a first end 208 of suture material 207 can be tied off or otherwise suitably secured to disc-shaped member 206 as shown in FIG. 12B.

Graft device 200 is deployable so that graft body distal portion 202 extends from a fistula opening, and graft body proximal portion 203 resides within a fistula tract extending from this opening. In general, graft device 200 will be sized and shaped so that when cap-forming portion 205 is generally uncompressed as shown in FIG. 12A, distal portion 202 can be passed through a secondary fistula opening, through a fistula tract, and out of a primary fistula opening. Thereafter, with plug body proximal portion 203 residing within a fistula tract 220 and plug body distal portion 202 extending from a fistula opening 222, the opposite end of suture material 207 can be pulled in a direction generally opposite this opening. This in turn will cause disc-shaped member 206 to exert a substantially even force across the end of graft body distal portion 202, causing cap-forming portion 205 to longitudinally compress while contacting patient tissue at and around fistula opening 222 to provide a capping member for blocking the opening. In some cases, it may be necessary to hold graft body proximal portion 203 steady in the tract while compressing cap-forming portion 205, for example, by hand or using a device of some sort.

In addition to the compressible cap-forming portion 205 depicted in FIGS. 12A and 12B, the present invention provides a number of other cap-forming arrangements where part of a plug can be compressed or otherwise similarly manipulated during deployment to provide a suitable fistula plug cap. In some embodiments, a graft body has one or more voids occurring therein, any one of which can extend from a surface of the graft body through all or part of the graft body to provide a cap-forming component. Additionally or alternatively, a graft body may include one or more voids not extending from a surface of the graft body but rather providing one or more hollow regions within the graft body. Any suitable configuration to promote and/or facilitate collapsing of the cap-forming portion or to otherwise cause or allow portions of the body to extend away from a central body region to provide a suitable capping arrangement are contemplated as within the scope of the present invention. In some aspects, a collapsible cap-forming portion is an attached mechanical device, e.g., one formed with metal and/or plastic. In other aspects, such a portion is formed with a material more easily collapsible than material forming other portions of a plug body. These and other adaptations for facilitating the formation of a cap will be recognized by the skilled artisan and are encompassed by the present invention.

The capping members described herein can exhibit a variety of shapes and configurations. In some instances, a capping member includes a resilient wire frame or other similar frame or frame-like support device. These devices can, in some embodiments, be designed to move between a first device configuration and a second device configuration, for example, in the case of a frame that is compactable to a compacted, first condition, and when in this compacted condition, is then expandable to an expanded, second condition. In forms where a frame has the capacity to expand, these frames can include those that are considered self-expanding and those that require at least some manipulation in order to expand.

Figure 13A:
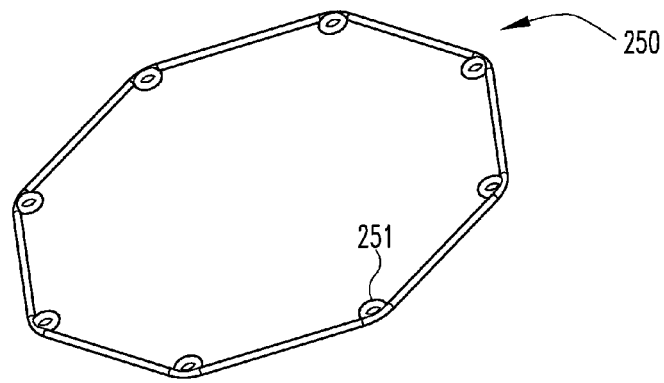
FIG. 13A is a perspective view of a support frame useful in the present invention.
Figures 13B, 13C:
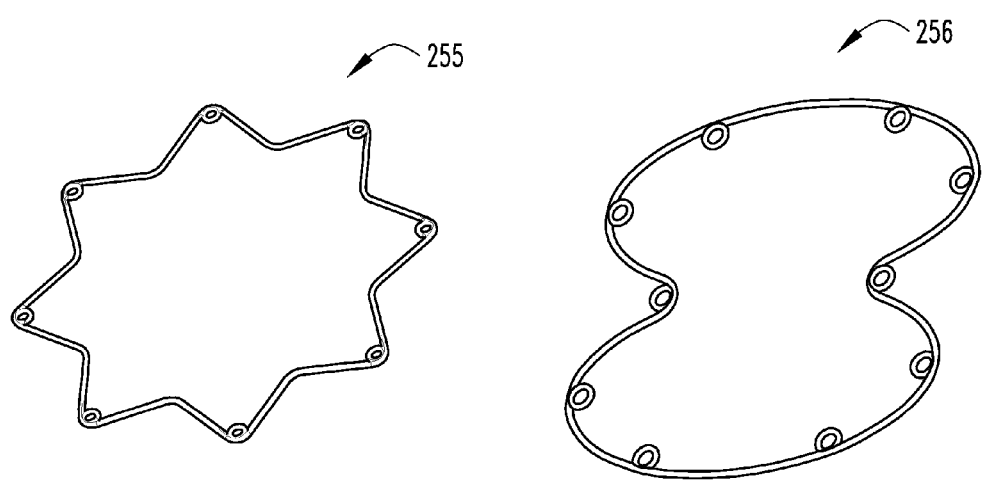
FIG. 13B is a perspective view of another support frame useful in the present invention.
FIG. 13C is a perspective view of yet another support frame useful in the present invention.

With reference now to FIG. 13A, shown is a support frame 250 which can be incorporated into a grafting device of the invention. Support frames of this sort and other similar devices useful in the present invention can be constructed using one or more pieces of superelastic wire or any of a variety of other suitable materials described herein or otherwise known to those skilled in the art. In this particular embodiment, support frame 250 includes a single piece of Nitinol wire having a plurality of sides and bends interconnecting adjacent sides. Bends of this sort can include coils, fillets, or other suitable configurations, for example, those designed to reduce stress and fatigue. Support frame 250 incorporates optional bend adaptations 251 having apertures occurring therein as generally shown. The single piece of wire is preferably joined by an attachment mechanism, such as a piece of cannula and solder, to form a closed circumference frame. While a preferred frame embodiment is an eight-sided polygon such as that shown in FIG. 13A, other shapes having rectilinear and/or curvilinear components are contemplated as well, for example, other polygonal shapes having three, four, five, six, seven or any suitable number of sides. Illustratively, two additional support frame embodiments 255 and 256 are shown in FIGS. 13B and 13C, respectively.

Support frame 250, which is shown in a relaxed condition in FIG. 13A, is a resilient device. Thus, the frame can be deformed (e.g., collapsed, compressed, etc.) from this relaxed, first condition to a deformed, second condition. In this deformed, second condition, the resilient frame is then poised to essentially return to its relaxed, first condition. Illustratively, support frame 250 can be compressed into a compressed condition (e.g., by folding one or more times and/or rolling portions of the frame) for positioning in a delivery device lumen having a relatively smaller diameter than that which the frame could otherwise fit in its relaxed condition. In this compressed condition, the frame then has the ability to self-expand essentially back to its prior, relaxed condition upon being removed from the delivery device lumen.

Figure 14:
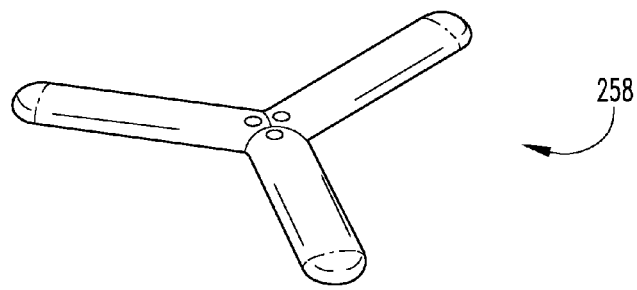
FIG. 14 is a perspective view of another support frame useful in the present invention.

FIG. 14 is a perspective view of another capping member 258 according to the present invention. A capping member of this sort can be attached to or otherwise joined with any of the elongate plug members described herein. In a preferred embodiment, capping member 258 is formed with a resorbable material, and is flexible so that it can be folded or otherwise condensed for positioning in a delivery device lumen. Capping member 258 includes a plurality of apertures in a centrally-located region, which may be useful for attaching capping member to a plug member.

In a preferred embodiment, a capping member includes a support frame and a deformable covering material. The support frame and covering material can each be formed with one or more of a variety of materials. Illustratively, a support frame formed with a resilient material (e.g., Nitinol) can be combined with a sheet-form resorbable material, and in some cases, a multilayered remodelable material, wherein this combination provides a suitable arrangement for blocking, and in some cases sealing off, a fistula opening. Arrangements of this sort include but are not limited to capping members that include a support frame that can lie in a single, generally flat plane, and a sheet-form deformable covering material extending between peripheral regions of the support frame, although a variety of other capping member shapes and configurations are contemplated as within the scope of the present invention as well.

When present, a covering material can be attached to or otherwise suitably associated with a support device in a variety of manners including some that involve bonding and/or mechanically fastening the covering material to the device. In some cases, an edge of a covering material is folded over a frame segment and attached to another portion of the material to provide a sleeve or other channel-like adaptation for retaining the covering material in association with the support frame. Certain embodiments of the invention provide capping members including an expandable frame member associated with a full or partial covering of material on one or more surfaces of (e.g., an inner and/or outer surface) of the expandable frame member. In some embodiments, the covering material is associated in a unique manner with the expandable frame member. For example, the covering material may be contoured snugly around or completely embed elements of the expandable frame member to assist in maintaining the attachment of the covering material to the expandable frame member. This may avoid, reduce, or simplify the need for other mechanical attachments, such as sutures, to hold the covering material to the expandable frame member. It may also in some forms provide a unique, relatively fixed association of the covering material with the expandable frame member or elements thereof, even during contraction and/or expansion of the frame. In some cases, a somewhat flexible material is desirably positioned around a frame, and then the material is physically, chemically and/or otherwise treated (e.g., lyophilized) so that the material becomes less flexible for maintaining the material in association with the frame.

Figure 15:
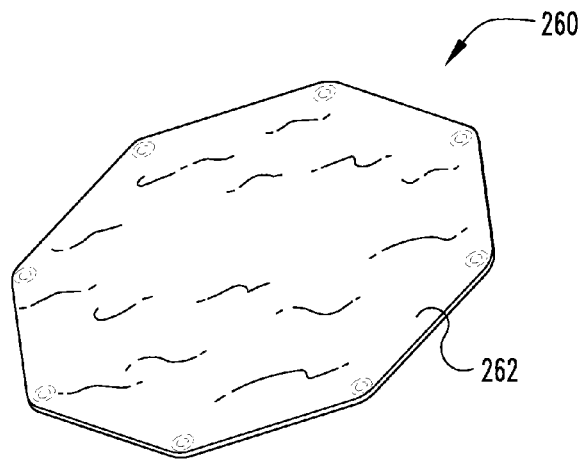
FIG. 15 provides a perspective view of a capping member of the present invention.

In some cases, a flexible covering material that is pulled taught along a collapsible support frame can fold and/or roll along with a frame as it collapses, and upon the frame returning to its prior shape, can also essentially return to its prior condition to again be pulled taught. Referring now to FIG. 15, shown is a capping member 260 that incorporates the support frame from FIG. 13A. Capping member 260 additionally includes a deformable covering material 262 attached to and extending between opposing, peripheral edges of the frame. In a preferred embodiment, capping member 260 will generally be sized and configured so that when positioned over a fistula opening in a bodily structure wall (e.g., a primary fistula opening in an alimentary canal wall), outer regions of the capping member (i.e., those including the support frame) extend beyond the opening along the bodily structure wall and contact portions of the bodily structure wall adjacent to the opening, and inner regions of the capping member cover and block the opening.

In some cases, a capping member such as capping member 260 will include an elongate device (e.g., a suture, plug member, etc.) extending therefrom. For example, an elongate plug can be sutured, glued or otherwise attached to covering material 262 in a region of the material that is centrally located relative to the support frame perimeter. In this manner, the device can be positioned in a patient such that capping member 260 is positioned over a fistula opening, and the elongate plug member extends into a fistula tract extending from this opening. In this position, the elongate plug member can be pulled away from the capped fistula opening such that portions of deformable covering material 262 are drawn into the fistula tract. Desirably, support frame 250 provides an anchor of sorts for capping member 260 so that as inner regions of covering material 262 are drawn into the fistula tract, support frame 250 and outer regions of covering material 262 remain outside of the fistula tract. In some cases, when a sufficiently flexible covering material is pulled in this manner, portions of the covering material can deform to provide a convex or other similar surface for contacting patient tissue at the fistula opening to seal or substantially seal off the opening.

Figure 16A:
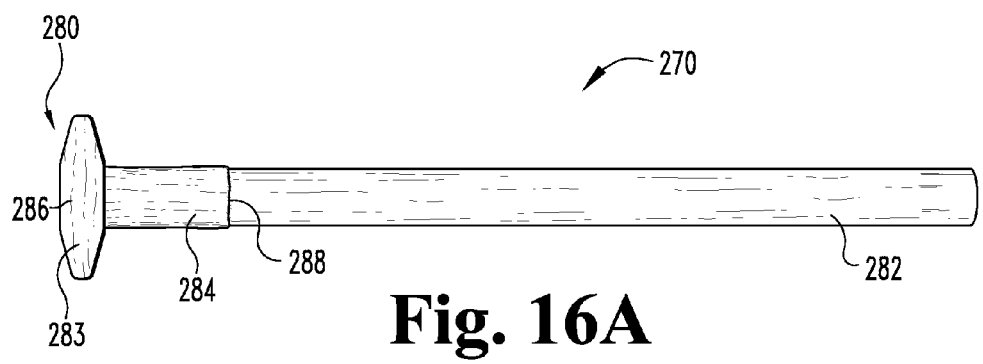
FIG. 16A is a perspective view of a medical graft device of the invention.
Figure 16B:
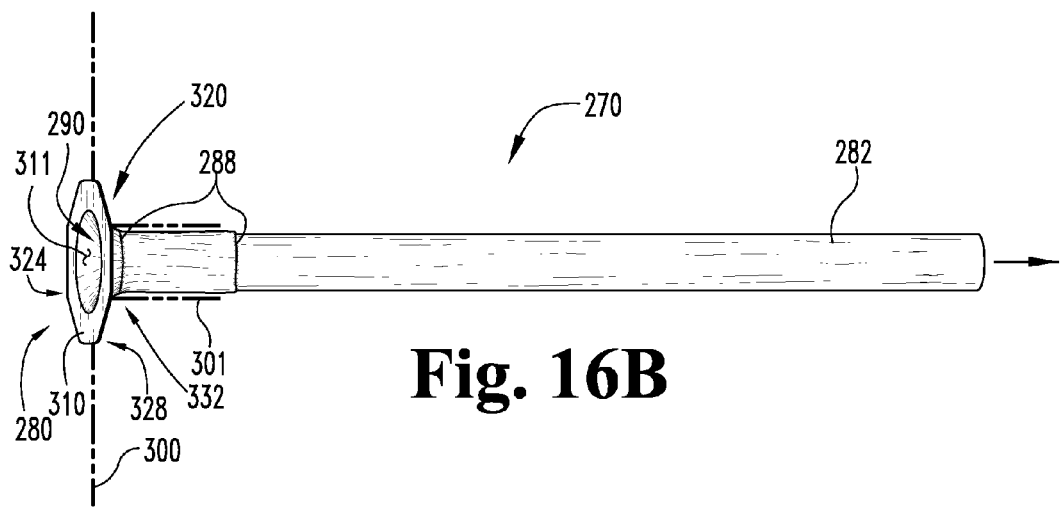
FIG. 16B shows the medical graft device of FIG. 16A implanted within a patient.

FIGS. 16A and 16B show a medical graft device 270 of the present invention that includes a capping member 280 and a generally cylindrical, elongate plug member 282 extending from this capping member. Plug member 282 is configured to extend into and fill at least a portion of a fistula tract, and its dimensions including its length can vary, with those skilled in the art recognizing suitable plug dimensions for a particular application. In some cases, a plug length is provided for extending through an entire fistula tract up to about 15 cm or longer, although such a plug could be cut to size as desired to fit all or a portion of a particular tract. As well, elongate plug member 282 can be formed with one or more of a variety of materials, and in some preferred embodiments, is formed with a rolled sheet-form material such as but not limited to a single- or multi-layered naturally-derived material (e.g., a collagenous ECM material). Capping member 280, which includes a deformable covering material 283, is similar to that shown in FIG. 14 except that it additionally includes a sheath portion 284 extending away (in a generally perpendicular direction) from a centrally-located region of its bottom surface. Capping member 280 includes a top surface 286. Sheath portion 284 is configured to be positioned over and extend along at least a segment of plug member 282 as generally shown in FIG. 16A. A plurality of sutures 288 attach sheath portion 284 to plug member 282, although a variety of other attachments means are contemplated as within the scope of the present invention.

A capping member sheath portion useful in the invention can be formed separately from, and then subsequently united with, the remainder of a capping member, or alternatively, can be formed as part of an existing capping member component. In this particular embodiment, sheath portion 284 comprises a portion of covering material 282 extending away from the remainder of the capping member. Illustratively, a sheath portion of this sort can be formed by providing a covering material sufficiently sized to be wrapped around a support frame with enough material left over on one side to form a sheath or sheath-like capping member component. In some cases, a somewhat flexible material is positioned around a frame in such a manner, and then the material is physically, chemically and/or otherwise treated (e.g., lyophilized) so that the material becomes less flexible for maintaining the material in the desired configuration.

Referring again to FIG. 16B, in some modes of use, graft device 270 is implanted within a patient such that capping member 280 is positioned over a fistula opening 290 occurring in a bodily structure wall 300, and elongate plug member 282 extends into a fistula tract 301 extending from this opening. In this position, plug member 282 can be pulled in the direction of the arrow shown (i.e., away from the capped fistula opening) such that portions of deformable covering material 283 are drawn into the fistula tract as generally shown. In an alternative embodiment, graft device 270 incorporates a tether extending from elongate plug member 282 (e.g., away from the end opposite capping member 280), which may be useful in manipulating the position the device at certain points during delivery. A tether of this sort may be a suture (e.g., a 2-0 vicryl suture) embedded within, attached to or otherwise associated with plug member 282.

Desirably, the support frame will be sized and configured so that it remains outside of the fistula tract (e.g., along the bodily structure wall in an area extending a suitable distance beyond the fistula opening) even when a considerable amount of pulling force is applied to plug member 282. In this manner, when capping member 280 is deformed as shown in FIG. 16B, the support frame and an externally remaining portion 310 of the covering material will remain outside of the fistula tract, while a portion of the covering material that previously (i.e., prior to deformation) resided outside of the fistula tract will now reside within the fistula tract to provide an internalized covering material portion 311. In some forms, the capping member is deformed so that portions of the covering material very snugly conform to patient tissue at the fistula opening in a generally non-planar condition such as a cupping or cup-like arrangement. For example, as illustrated in FIG. 16B, capping member 280 may comprise a plug-facing/proximally-facing surface 320 and a plug-opposing/distally-facing surface 324 opposite the plug-facing/proximally-facing surface 320, the plug-opposing/distally-facing surface 324 being a distal-most surface of the graft device 270. The plug-facing/proximally-facing surface 320 has a peripheral region 328 and an inner region 332 inside the peripheral region 328. The peripheral region 328 of the plug-facing/proximally-facing surface 320 is configured to contact portions of the bodily structure wall adjacent to the primary opening. The plug member 282 can then be secured in position, e.g., using one or more sutures to patient tissue, to retain the conforming condition of the capping member.

Graft device 270 and other similar inventive devices are particularly suitable for treating enterocutaneous and other gastrointestinal fistulae, although such devices can be adapted to treat a variety of other fistulae as well. These devices can be implanted in any suitable manner. In a preferred embodiment, graft device 270 is placed with the aid of a delivery sheath or other similar delivery device, for example, a splittable sheath as discussed in more detail below. In one mode of operation, the distal end of a wire guide is passed into an enterocutaneous fistula tract through a secondary fistula opening and toward a primary fistula opening under fluoroscopic guidance. The wire is advanced until its distal end enters the alimentary canal through the primary opening. Thereafter, the distal end of an over-the-wire dilator-sheath combination is advanced through the tract in a similar manner, for example, until the sheath is positioned at or just beyond the primary opening. The dilator is then removed, leaving the sheath (e.g., a check-flow sheath) and potentially also the guidewire in the tract. In some cases, the wire guide is removed with the dilator. Then, a suitably sized and shaped graft device such as graft device 270 is loaded into the sheath through its proximal end, for example, with the capping member 280 in a compressed condition (e.g., folded one or more times and/or rolled) entering the sheath first, and elongate plug member 282 following. The plug member may then be fully pushed into the sheath by hand. The capping member, in a compressed condition, is poised to return to its expanded condition upon being removed from the delivery device lumen.

Next, an over-the-wire pusher is introduced into the sheath proximal end and advanced toward the sheath distal end until at least a portion of the graft device is desirably pushed from the sheath distal end (e.g., with capping member 280 in an expanded condition and extending a distance into the alimentary canal). In some cases, the capping member and/or plug member will incorporate a device or material to aid in imaging the device during delivery. Illustratively, a stainless steel button or other similar device may be attached to the end of the plug member near the capping member. As well, a capping member support frame can be formed with a radiopaque material. Alternatively, a support frame can be formed with a resorbable material such as a collagenous ECM material (e.g., SIS), polycaprolactone, polyhydroxyalkanoates- or PHA polymers, etc. with a radiopaque marker attached.

Then, the pusher can be placed in contact with the plug member 282 to provide back pressure, while the delivery sheath is removed, thus maintaining desirable positioning of the device inside the tract. After the sheath and pusher are removed, plug member 282 can be manipulated to achieve a desired deformation of capping member 280, for example, as described above. With capping member 280 desirably deformed, plug member 282 can then be secured in place (e.g., sutured or otherwise fixed to patient tissue at and/or around the secondary fistula opening) to maintain the capping member in this deformed condition. In some cases, the plug member will extend a distance out of the secondary opening when the capping member is deformed. This portion may optionally be trimmed off before or after the plug is secured in place. Although not necessary to broader aspects of the present invention, in the current embodiment, plug member 282 is directly or indirectly attached to the underside of the material defining the capping member top surface 286, and in this regard, internalized covering material portion 311 includes some of the material defining this surface. In one aspect, a support frame is attached to a covering material with resorbable sutures, allowing the frame to separate from the remainder of the graft device after a certain amount of time following initial plug deployment, and pass through and out of the alimentary canal.

In some preferred embodiments, care is taken to not block or otherwise close the secondary opening to facilitate drainage of the tract following the implantation procedure, for example, during remodeling when a remodelable material is utilized in the plugging assembly. Of course, it will be understood that the steps described above can occur in any suitable order as will be recognized by those skilled in the art. For example, a graft device may be preloaded into a delivery device before the delivery device is positioned in a fistula tract. In some cases, when a delivery system component (e.g., a wire guide, dilator, pusher, etc.) is deemed not necessary for a particular delivery application, this component will be excluded from the delivery system and any associated methods of delivery.

Delivery devices useful in certain aspects of the present invention have a lumen communicating with a distal, open end. This "leading" distal end is configured to pass into passageways and other open spaces in the body. Although not necessary to broader aspects of the invention, this distal end, or any portion thereof, may be particularly configured to enhance travel of the device through certain body passageways, for example, including a tapered portion and/or having a dome-shaped or otherwise rounded tip. Accordingly, such devices can exhibit any suitable size, shape and configuration for performing the functions described herein, while avoiding substantially cutting or tearing surrounding soft tissues.

Where a delivery device is used to deliver a graft device into a fistula tract, such a device may have a length of about 2 inches to about 12 inches, more typically about 3 inches to about 9 inches, and even more typically about 4 to about 8 inches. Also, these devices may have an outside diameter of about 0.3 mm to about 3.2 mm, more typically about 0.5 to about 3.0 mm, and even more typically about 1.0 mm to about 2.5 mm.

In some embodiments, a delivery device is rigid or substantially rigid, and is configured to be generally straight, for example, for use in treating certain simple or straight fistulae. Alternatively, delivery devices useful in the invention can be configured to include one or more portions that are curvilinear, bent, or otherwise suitably shaped. In certain aspects, the distal end of a delivery device is curved to a degree to allow for easier passage of the distal end through a complex fistula, e.g., a horseshoe fistula, and/or through the primary fistula opening and into the alimentary canal. In some forms, a delivery device is composed of a malleable material such as but not limited to a woven or spirally-configured metal or alloy material, or a plastic (hydrocarbon-based) material, which may be bent to the necessary angle or curvature, for example, to allow passage through a fistula tract. The shape of such a delivery device may be adjusted at certain intervals of the procedure so as to allow the delivery device to pass further and further into the fistula tract, until the primary opening is identified. In some forms, the delivery device is generally straight in a relaxed condition but can flex to adapt to contours during passage.

In this regard, delivery devices, when used in the invention, can be formed with one or more of a variety of materials. A particular material may be selected to take advantage of one or more of its properties such as but not limited to its weight, durability, flexibility, etc. For example, a device may comprise a material having properties that allow the device to traverse a body passageway without buckling or kinking or causing unacceptable damage to soft tissues defining the passageway. Illustratively, the device, or selected portions thereof (e.g., the distal end), can exhibit a degree of flexibility. In this regard, a delivery device, or any portion thereof, may be rigid, malleable, semi-flexible, or flexible. In certain embodiments, an endoluminally advancable device is particularly adapted for moving through and into body passages that angulate sharply or curve abruptly such as when traversing the alimentary canal, passing through and into a fistula opening, traversing a fistula tract, etc. In some of these embodiments, the device is configured to be directable or steerable through the passageway, and therefore, exhibits desirable characteristics, e.g., sufficient stiffness, to allow an operator to apply an adequate degree of ante-grade force to the device to allow it to traverse a passageway in a desirable manner.

Suitable materials for forming delivery devices or device components of the invention can include but are not limited to metallic materials including stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, the delivery device can include material in the form of yarns, fibers, and/or resins, e.g., monofilament yarns, high tenacity polyester, and the like. A delivery device can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon.

In some forms, a flexible delivery device will incorporate one or more adaptations for facilitating removal of the device from the body during a delivery procedure. Illustratively, a protective sleeve can incorporate scores, thinner portions, and other openings and non-openings that weaken a portion of the sleeve to facilitate a splitting operation in removing the sleeve from the tract. Such a weakened portion may include any suitable means for facilitating tearing or breaking along the area. In certain beneficial forms, a protective sleeve is controllably separable longitudinally into two or more pieces for removal, for example, as occurs in Peel-Away® catheters available from Cook Incorporated, Bloomington, Ind., USA. Such an apparatus with a separable sleeve is particularly useful in treating fistulae that have a secondary opening in the outer skin surface and a primary opening that is relatively difficult to access other than through the fistula tract, e.g. as occurs in a large percentage of enterocutaneous fistulae. In one aspect, a delivery system comprises a suitably sized and configured inner dilator, a splittable sheath, and a "pusher" device that is translatable through the sheath, wherein all of these can be received over an emplaced guidewire.

Additionally, the medical graft products of the invention can be modified before, during, and/or after deployment. Illustratively, a product may be cut, trimmed, sterilized, and/or treated (e.g., brought into contact, impregnated, coated, etc.) with one or more desirable compositions, such as any of those previously disclosed herein, e.g., anticoagulants (e.g., heparin), growth factors or other desirable property modifiers. In certain aspects, following deployment of a graft body in accordance with the present invention, one or more portions of the body are trimmed off or otherwise removed, for example, material protruding from the primary opening and/or any secondary opening.

Further, the fistula treatment methods described herein can be used to close one or more fistula during a given medical procedure. Also, methods of the invention can be used to treat complex fistula. For multiple fistula, multiple medical graft products can be engrafted until all the fistula have been addressed. In cases of complex fistula, for example a horse-shoe fistula, there may be one primary opening and two or more fistula tracts extending from that opening. In such instances, a medical graft product may be configured with a graft body including one capping member and two or more elongate plug members. Each plug member can be drawn into the primary opening, and thereafter into one of the fistula tracts extending therefrom. Each of the elongate plug members and/or the capping member of the body can be secured by sutures and/or an adhesive, if necessary, and any excess material can be trimmed.

Additional embodiments of the invention provide methods for treating fistulas that involve the use of flowable remodelable extracellular matrix material. In such embodiments, the flowable material can be used to fill openings and/or tracts of fistulas, including anorectal or other alimentary fistulas, and promote tissue ingrowth to close the fistulas. In this regard, the flowable material can be delivered in any suitable fashion, including for example forcible ejection from cannulated members such as catheters, sheaths, or needles. Suitable flowable, remodelable ECM materials for use in this aspect of the invention can be prepared, for example, as described in U.S. Pat. Nos. 5,275,826 and 5,516,533 or in International Publication No. WO2005020847 (Cook Biotech Incorporated) published Mar. 10, 2005, which are each hereby incorporated by reference in their entirety. Such flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth. Flowable ECM materials can also be used in conjunction with graft body devices as described herein, or implant bodies having other constructions. Implanted bodies can, for example, be provided at one or more locations of the fistula, e.g. within the primary opening, and can act as a confining barrier to an amount of flowable ECM material introduced against the barrier and filling the tract of the fistula to promote healing.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical graft device useful for treating a fistula having at least a primary opening in a bodily structure wall and a fistula tract extending from the primary opening, the medical graft device comprising:
    a biocompatible graft body including a capping member and an elongate plug member, the capping member comprising a plug-facing surface and a plug-opposing surface opposite the plug-facing surface, the plug-opposing surface being a distal-most surface of the medical graft device; the plug-facing surface having a peripheral region and an inner region inside the peripheral region; the peripheral region of the plug-facing surface configured to contact portions of the bodily structure wall adjacent to the primary opening and including a support frame supporting a deformable covering material, the elongate plug member coupled to the deformable covering material and extending from the inner region of the capping member and including a rolled sheet material providing a volumetric body configured to fill at least a portion of the fistula tract; and a tether extending in a proximal direction away from a proximal end of the elongate plug member and having a length sufficient to extend through the fistula tract so as to be useful to pull the graft body into position, the tether not being part of the rolled sheet material;

wherein the inner region of the capping member is deformable from a first condition to a second condition by pulling the elongate plug member in a direction away from the capping member; wherein in the first condition the inner and peripheral regions define a generally flat surface that is substantially perpendicular to a longitudinal axis of the plug member; and wherein in the second condition the peripheral region defines a generally flat surface substantially perpendicular to the longitudinal axis of the plug member and the inner region of the plug-facing surface defines a convex surface and the plug-opposing surface of the capping member defines a corresponding concave surface.

2. The medical graft device of claim 1, wherein the deformable covering material comprises a naturally derived material.

3. The medical graft device of claim 1, wherein the deformable covering material comprises a non-naturally derived material.

4. The medical graft device of claim 1, wherein the deformable covering material comprises a synthetic polymeric material.

5. The medical graft device of claim 1, wherein the deformable covering material comprises a collagenous material.

6. The medical graft device of claim 1, wherein the deformable covering material comprises a remodelable material.

7. The medical graft device of claim 1, wherein the deformable covering material comprises an extracellular matrix material.

8. The medical graft device of claim 7, wherein said extracellular matrix material comprises submucosa.

9. The medical graft device of claim 8, wherein said submucosa comprises porcine submucosa.

10. The medical graft device of claim 7, wherein said extracellular matrix material comprises small intestine submucosa, urinary bladder submucosa, or stomach submucosa.

11. The medical graft device of claim 7, wherein said extracellular matrix material comprises serosa, pericardium, dura mater, peritoneum, or dermal collagen.

12. The medical graft device of claim 1, wherein the support frame comprises a single piece of wire.

13. The medical graft device of claim 1, wherein the support frame comprises a plurality of interconnected wire pieces.

14. The medical graft device of claim 1, wherein the support frame is formed with Nitinol wire.

15. The medical graft device of claim 1, wherein the support frame includes peripheral segments lying within a single, generally flat plane.

16. The medical graft device of claim 15, wherein the peripheral segments are interconnected to provide a closed circumference frame.

17. The medical graft device of claim 16, wherein the deformable covering material extends between the peripheral segments of the support frame.

18. The medical graft device of claim 1, wherein the support frame includes a rectilinear segment.

19. The medical graft device of claim 1, wherein the support frame includes a curvilinear segment.

20. The medical graft device of claim 1, wherein the support frame is compactable to a compacted first condition permitting its passage through the fistula tract and the primary opening, and wherein the support frame in the compacted first condition is self-expandable to an expanded second condition effective to inhibit its passage back through the primary opening.

21. The medical graft device of claim 1, wherein the deformable covering material is sutured to the support frame.

22. The medical graft device of claim 1, wherein the deformable covering material is bonded to the support frame.

23. The medical graft device of claim 1, wherein the support frame is embedded within portions of the deformable covering material.

24. The medical graft device of claim 1 adapted to treat enterocutaneous fistulae.

25. The medical graft device of claim 1, wherein the capping member has a portion configured to extend into the primary opening when the medical graft device is implanted.

26. The medical graft device of claim 1, wherein the elongate plug member is of a length sufficient to extend from the capping member through the fistula tract and out of a secondary opening in the fistula when the medical graft device is implanted.

27. The medical graft device of claim 1, wherein the elongate plug member exhibits a generally cylindrical shape.

28. The medical graft device of claim 1, wherein the elongate plug member includes a tapered portion.

29. The medical graft device of claim 1, wherein the elongate plug member comprises at least one layer of compliant material.

30. The medical graft device of claim 29, wherein the at least one layer of compliant material is deformable upon impingement by soft tissue surrounding the fistula tract and is sized and shaped so as to be deformable to a three-dimensional volumetric body.

31. The medical graft device of claim 29 wherein the elongate plug member comprises two to ten layers of compliant material.

32. The medical graft device of claim 1, wherein the rolled sheet material provides spiral layers.

33. The medical graft device of claim 32, wherein the spiral layers are compressed and bonded so as to form a substantially unitary structure.

34. The medical graft device of claim 1, wherein the elongate plug member has a cross sectional dimension of from 3 mm to 20 mm.

35. The medical graft device of claim 1, wherein the elongate plug member has a cross sectional dimension of from 5 mm to 15 mm.

36. The medical graft device of claim 1, wherein the elongate plug member comprises a non-naturally derived material.

37. The medical graft device of claim 1, wherein the elongate plug member comprises a naturally derived material.

38. The medical graft device of claim 1, wherein the elongate plug member comprises a collagenous material.

39. The medical graft device of claim 1 incorporating a radiopaque element.

40. The medical graft device of claim 1, wherein the elongate plug member has a length in the range of about 1 inch to about 8 inches.

41. The medical graft device of claim 1, wherein the elongate plug member has a length in the range of about 2 inches to about 4 inches.

42. The medical graft device of claim 1, wherein the elongate plug member is connected to the deformable covering material.

43. A medical graft device useful for treating a fistula having at least a primary opening in a bodily structure wall and a fistula tract extending from the primary opening, the medical graft device comprising:
a biocompatible graft body including a capping member, an elongate plug member, and a suture extending from the capping member, the elongate plug member including a rolled sheet material, the capping member including a support frame supporting a deformable covering material, the deformable covering material having a proximally-facing surface and a distally-facing surface opposite the proximally-facing surface; the distally-facing surface being a distal-most surface of the medical graft device; the proximally-facing surface comprising a peripheral region and an inner region inside the peripheral region, the inner region being deformable independently of the peripheral region between a first condition and a second condition by pulling the suture in a direction away from the capping member, the inner region in the first condition defining a generally flat surface and in the second condition defining a convex surface arranged for contacting patient tissue at the primary opening, the convex surface having an externalized material portion and an internalized material portion, the externalized material portion configured to reside externally of the fistula tract when the graft device is implanted and the covering material is deformed, and the internalized material portion configured to reside within the fistula tract when the graft device is implanted and the covering material is deformed;
wherein the suture is configured to extend in proximal direction beyond a proximal end of the elongate plug member through the fistula tract when the graft device is implanted and is actuatable to convert the inner region of the covering material from the first condition to the second, deformed condition, the suture not being part of the elongate plug member; and
wherein the distally-facing surface defines a concave surface that corresponds to the convex surface of the inner region of the proximally-facing surface in the second condition.

44. The medical graft device of claim 43, wherein the deformable covering material comprises a non-naturally derived material.

45. The medical graft device of claim 43, wherein the deformable covering material comprises a collagenous material.

46. The medical graft device of claim 43, wherein the support frame is configured to reside externally of the fistula tract and contact portions of the bodily structure wall adjacent to the primary opening when the graft device is implanted and the covering material is deformed.

47. The medical graft device of claim 46, wherein the support frame is compactable to a compacted first condition permitting its passage through the fistula tract and the primary opening, and wherein the support frame in the compacted first condition is self-expandable to an expanded second condition effective to inhibit its passage back through the primary opening.

48. The medical graft device of claim 43, wherein the suture is embedded within the elongate plug member.

49. A medical product, comprising:
a medical graft device useful for treating a fistula having at least a primary opening in a bodily structure wall and a fistula tract extending from the primary opening, the medical graft device comprising:
a biocompatible graft body including a capping member and an elongate plug member, the capping member comprising a plug-facing surface and a plug-opposing surface opposite the plug-facing surface, the plug-opposing surface being a distal-most surface of the medical graft device; the plug-facing surface having a peripheral region and an inner region inside the peripheral region; the peripheral region of the plug-facing surface configured to contact portions of the bodily structure wall adjacent to the primary opening and including a support frame supporting a deformable covering material, the elongate plug member coupled to the deformable covering material and extending from the inner region of the capping member and including a rolled sheet material providing a volumetric body configured to fill at least a portion of the fistula tract;
a tether extending in a proximal direction away from a proximal end of the elongate plug member and having a length sufficient to extend through the fistula tract so as to be useful to pull the biocompatible graft body into position, the tether not being part of the rolled sheet material; and
a sealed package enclosing the medical graft device;
wherein the inner region of the capping member is deformable from and between a first condition and a second condition by pulling the elongate plug member in a direction away from the capping member; wherein in the first condition the inner and peripheral regions define a generally flat surface that is substantially perpendicular to a longitudinal axis of the elongate plug member; and wherein in the second condition the peripheral region defines a generally flat surface substantially perpendicular to the longitudinal axis of the elongate plug member, the inner region of the plug-facing surface defines a convex surface, and the plug-opposing surface defines a corresponding concave surface.

50. A medical graft device useful for treating a fistula having at least a primary opening in a bodily structure wall and a fistula tract extending from the primary opening, the medical graft device comprising:
a biocompatible graft body including a capping member, an elongate plug member and a suture extending from the capping member, the elongate plug member including a rolled sheet material, the capping member including a support frame supporting a deformable covering material, the deformable covering material deformable between a first condition and a second condition by pulling the suture in a direction away from the capping member and the deformable covering material having a peripheral region and an inner region, the inner region positioned inside the peripheral region and being deformable independently of the peripheral region;

wherein in the first condition a proximally-facing surface and a distally-facing surface of the inner region each define a generally flat surface and in the second condition the proximally-facing surface of the inner region defines a convex surface arranged to contact patient tissue at the primary opening;

wherein the suture is configured to extend in proximal direction beyond a proximal end of the elongate plug member through the fistula tract when the graft device is implanted and is actuatable to convert the covering material from the first condition to the second condition, the suture not being part of the elongate plug member; and wherein the distally-facing surface is a distal-most surface of the medical graft device.

51. The medical graft device of claim 50, wherein the support frame includes peripheral segments lying within a single, generally flat plane.

52. The medical graft device of claim 51, wherein the peripheral segments are interconnected to provide a closed circumference frame.

53. The medical graft device of claim 52, wherein the deformable covering material extends between the peripheral segments of the support frame.

54. The medical graft device of claim 50, wherein the support frame is compactable to a compacted first condition permitting its passage through the fistula tract and the primary opening, and wherein the support frame in the compacted first condition is self-expandable to an expanded second condition effective to inhibit its passage back through the primary opening.

55. The medical graft device of claim 50, wherein the suture is embedded within the elongate plug member.

56. A medical graft device useful for treating a fistula having at least a primary opening in a bodily structure wall and a fistula tract extending from the primary opening, the medical graft device comprising:

a biocompatible graft body including a capping member and an elongate plug member, the capping member comprising a deformable covering material having a plug-facing surface, a plug-opposing surface, a peripheral region and an inner region; the peripheral region configured to contact portions of the bodily structure wall adjacent to the primary opening and including a resilient wire support frame supporting portions of the deformable covering material, the inner region positioned inside the peripheral region and coupled to the elongate plug member extending from the capping member; and a tether extending away from a proximal end of the elongate plug member and having a length sufficient to extend through the fistula tract so as to be useful to pull the graft body into position;

wherein the capping member is deformable between a first condition and a second condition different from the first condition by pulling the elongate plug member in a direction away from the capping member; and wherein in the second condition the peripheral region defines a generally flat surface and the plug-facing surface of the inner region defines a convex surface and the plug-opposing surface defines a concave surface positioned proximally of the resilient wire support frame;

wherein the concave surface of the deformable covering material is part of a distal-most surface of the medical graft device;

wherein the elongate plug member exhibits a generally cylindrical shape.

57. The medical graft device of claim 56, wherein the resilient wire support frame includes peripheral segments lying within a single, generally flat plane.

58. The medical graft device of claim 57, wherein the peripheral segments are interconnected to provide a closed circumference frame.

59. The medical graft device of claim 58, wherein the deformable covering material extends between the peripheral segments of the resilient wire support frame.

60. The medical graft device of claim 1, wherein the tether is a suture.

61. The medical graft device of claim 60, wherein the suture is embedded within the elongate plug member.

* * * * *